(12) United States Patent
Birkmeyer et al.

(10) Patent No.: US 8,016,835 B2
(45) Date of Patent: Sep. 13, 2011

(54) RIGIDLY GUIDED IMPLANT PLACEMENT WITH CONTROL ASSIST

(75) Inventors: Paul Birkmeyer, Marshfield, MA (US); Christopher W. Sicvol, Durham, NC (US); Hassan Serhan, South Easton, MA (US); Sean Selover, Westport, MA (US); Ronald Naughton, Westfield, NJ (US); Nancy M. Sheehy, New York, NY (US)

(73) Assignee: DePuy Spine, Inc., Raynham, MA (US)

( * ) Notice: Subject to any disclaimer, the term of this patent is extended or adjusted under 35 U.S.C. 154(b) by 564 days.

(21) Appl. No.: 11/497,877

(22) Filed: Jul. 31, 2006

(65) Prior Publication Data

US 2007/0055291 A1 Mar. 8, 2007

Related U.S. Application Data

(63) Continuation-in-part of application No. 10/913,178, filed on Aug. 6, 2004.

(51) Int. Cl.
*A61B 17/58* (2006.01)
*A61B 17/60* (2006.01)
*A61F 2/00* (2006.01)

(52) U.S. Cl. .......................................................... 606/97

(58) Field of Classification Search .................... 606/19, 606/54, 58, 129, 130, 198, 253, 257, 87, 606/96, 104, 86 R, 97; 600/141, 142, 228, 600/229
See application file for complete search history.

(56) References Cited

U.S. PATENT DOCUMENTS

| 2,919,599 | A | * | 1/1960 | Milton et al. ............... 74/490.15 |
|---|---|---|---|---|
| 5,016,486 | A | | 5/1991 | Watson et al. |
| 5,184,601 | A | | 2/1993 | Putman |
| 5,212,720 | A | | 5/1993 | Landi et al. |
| 5,236,432 | A | | 8/1993 | Matsen, III et al. |
| 5,250,055 | A | | 10/1993 | More et al. |
| 5,397,323 | A | * | 3/1995 | Taylor et al. ................... 606/130 |
| 5,410,638 | A | | 4/1995 | Colgate et al. |
| 5,445,166 | A | | 8/1995 | Taylor |
| 5,808,665 | A | | 9/1998 | Green |
| 5,810,841 | A | | 9/1998 | McNeirney et al. |
| 5,814,038 | A | | 9/1998 | Jensen et al. |
| 5,855,583 | A | | 1/1999 | Wang et al. |
| 5,961,527 | A | * | 10/1999 | Whitmore et al. ............ 606/130 |
| 6,059,790 | A | | 5/2000 | Sand et al. |

(Continued)

FOREIGN PATENT DOCUMENTS

EP 0654244 B1 5/1995

(Continued)

*Primary Examiner* — Thomas C Barrett
*Assistant Examiner* — Sameh Boles
(74) *Attorney, Agent, or Firm* — Nelson Mullins Riley & Scarborough LLP

(57) ABSTRACT

A system for guiding an implant to an optimal placement within a patient includes a trajectory guide for guiding instruments along a selected trajectory and a trajectory fixation device for fixing the trajectory guide in a selected position. The trajectory guide defines a path configured to align with the selected trajectory. A movable support mounts the trajectory guide and selectively moves the trajectory guide to align the trajectory guide with the selected trajectory prior to fixing the trajectory guide in the selected position. The trajectory is aligned coarsely by hand, then the trajectory is aligned using a fine adjustment system. After fixing the trajectory guide, instruments can be inserted along the trajectory through the path defined by the trajectory guide.

12 Claims, 20 Drawing Sheets

U.S. PATENT DOCUMENTS

| | | | |
|---|---|---|---|
| 6,096,049 A | 8/2000 | McNeirney et al. | |
| 6,120,465 A | 9/2000 | Guthrie et al. | |
| 6,159,179 A | 12/2000 | Simonson | |
| 6,206,890 B1 | 3/2001 | Truwit | |
| 6,246,200 B1 | 6/2001 | Blumenkranz et al. | |
| 6,298,262 B1 | 10/2001 | Franck et al. | |
| 6,334,067 B1 | 12/2001 | Brabrand et al. | |
| 6,351,662 B1 | 2/2002 | Franck et al. | |
| 6,409,735 B1 * | 6/2002 | Andre et al. | 606/130 |
| 6,529,765 B1 | 3/2003 | Franck et al. | |
| 6,546,277 B1 | 4/2003 | Franck et al. | |
| 6,546,279 B1 | 4/2003 | Bova et al. | |
| 6,575,899 B1 | 6/2003 | Foley et al. | |
| 6,626,830 B1 | 9/2003 | Califiore et al. | |
| 6,725,080 B2 | 4/2004 | Melkent et al. | |
| 6,796,988 B2 | 9/2004 | Melkent et al. | |
| 6,837,892 B2 | 1/2005 | Shoham et al. | |
| 6,872,213 B2 | 3/2005 | Chakeres | |
| 6,921,406 B1 | 7/2005 | Chakeres | |
| 6,929,606 B2 | 8/2005 | Ritland | |
| 6,949,105 B2 | 9/2005 | Bryan et al. | |
| 6,951,538 B2 | 10/2005 | Ritland | |
| 2001/0027271 A1 | 10/2001 | Franck et al. | |
| 2002/0035321 A1 | 3/2002 | Bucholz et al. | |
| 2002/0038118 A1 * | 3/2002 | Shoham | 606/1 |
| 2002/0123668 A1 | 9/2002 | Ritland | |
| 2003/0149430 A1 | 8/2003 | Ferrante et al. | |
| 2003/0167061 A1 * | 9/2003 | Schlegel et al. | 606/130 |
| 2003/0187431 A1 | 10/2003 | Simonson | |
| 2003/0189351 A1 | 10/2003 | Nakayama et al. | |
| 2003/0236447 A1 | 12/2003 | Ritland | |
| 2004/0158260 A1 | 8/2004 | Blau et al. | |
| 2004/0176779 A1 | 9/2004 | Casutt et al. | |
| 2005/0033315 A1 | 2/2005 | Hankins | |
| 2005/0070789 A1 | 3/2005 | Aferzon | |
| 2005/0085714 A1 | 4/2005 | Foley et al. | |
| 2005/0101866 A1 | 5/2005 | Goodwin | |
| 2005/0113809 A1 | 5/2005 | Melkent et al. | |
| 2005/0132837 A1 | 6/2005 | Ben Horin et al. | |
| 2005/0149054 A1 | 7/2005 | Gorek | |
| 2005/0171557 A1 | 8/2005 | Shoham | |
| 2005/0171559 A1 | 8/2005 | Chakeres | |
| 2005/0216026 A1 | 9/2005 | Culbert | |
| 2006/0036264 A1 | 2/2006 | Selover et al. | |
| 2007/0055291 A1 | 3/2007 | Birkmeyer et al. | |

FOREIGN PATENT DOCUMENTS

| | | |
|---|---|---|
| EP | 1018963 B1 | 7/2000 |
| WO | WO-03/009768 A1 | 2/2003 |
| WO | WO-03/105659 A2 | 12/2003 |
| WO | WO-2004/100758 A2 | 11/2004 |
| WO | WO-2005/009215 A2 | 2/2005 |
| WO | WO-2005/032325 A2 | 4/2005 |

* cited by examiner

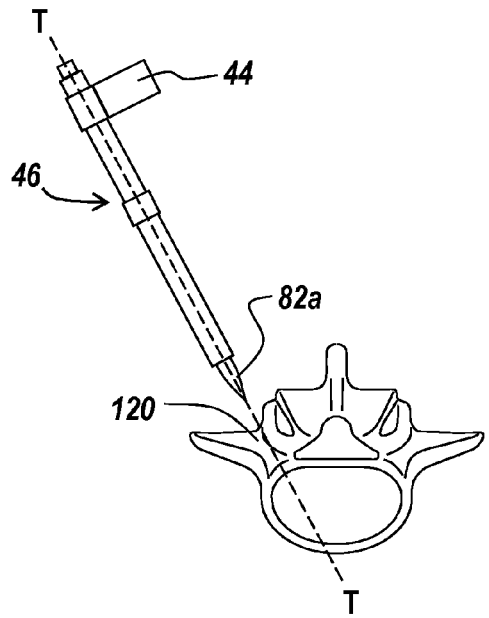
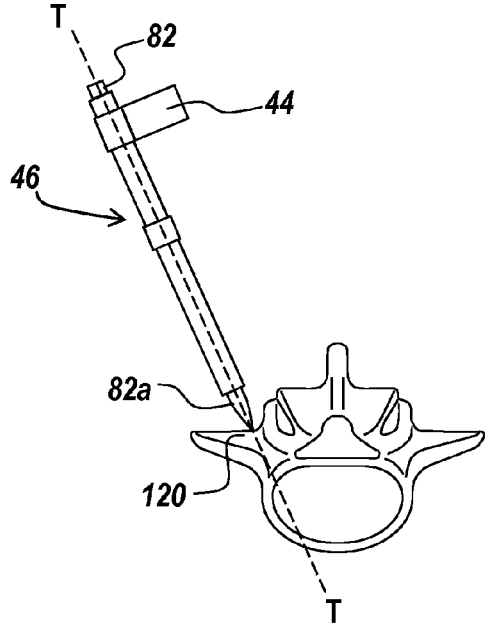
*Fig. 10A*  *Fig. 10B*
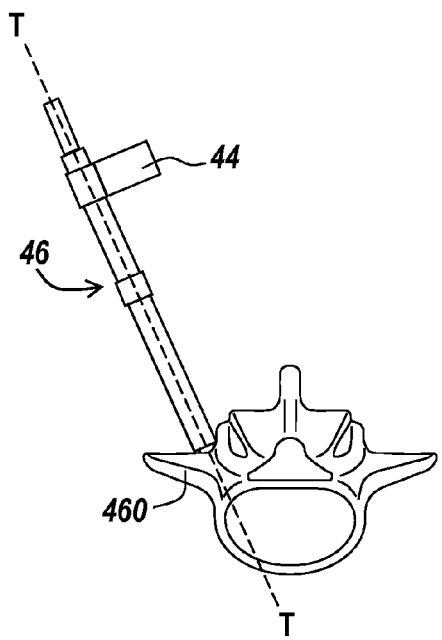
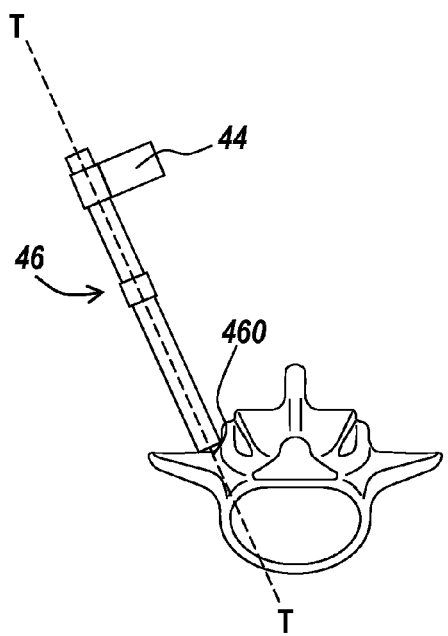
*Fig. 10C*  *Fig. 10D*

RIGIDLY GUIDED IMPLANT PLACEMENT WITH CONTROL ASSIST

RELATED APPLICATIONS

The present invention is a continuation-in-part of U.S. patent application Ser. No. 10/913,178 filed Aug. 6, 2004 and entitled RIGIDLY GUIDED IMPLANT PLACEMENT, the contents of which are herein incorporated by reference.

FIELD OF THE INVENTION

The present invention relates to spinal fixation devices used in orthopedic surgery. More particularly, the present invention relates to instrumentation and a method for the optimal placement of surgical implements and implants.

BACKGROUND OF THE INVENTION

Spinal fixation systems may be used in orthopedic surgery to align, stabilize and/or fix a desired relationship between adjacent vertebral bodies. Such systems typically include a spinal fixation element, such as a relatively rigid fixation rod or plate, extending along an axis along which the vertebral bodies are to be positioned and coupled to adjacent vertebrae by attaching the element to various anchoring devices, such as hooks, bolts, wires or screws. The spinal fixation element can have a predetermined contour that has been designed according to the properties of the target implantation site and, once installed, the spinal fixation element holds the vertebrae in a desired spatial relationship, either until desired healing or spinal fusion has occurred, or for some longer period of time.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone, which is the strongest part of the vertebrae. Such screws typically include a threaded shank that is adapted to be threaded into a vertebra, and a head portion having a spinal fixation element receiving element, which, in spinal rod applications, is usually in the form of a U-shaped slit formed in the head for receiving the rod. In many pedicle screws, the head is movable and preferably pivotable in all directions, relative to the shaft. The ability to move the head relative to the anchoring portion of the screw facilitates alignment and seating of a rod connecting a plurality of screws A set-screw, plug, cap or similar type of closure mechanism may be used to lock the rod into the rod-receiving portion of the pedicle screw. In use, the shank portion of each screw is then threaded into a vertebra, and once properly positioned, a fixation rod is seated through the rod-receiving portion of each screw and the rod may be locked in place by tightening a cap or similar type of closure mechanism to securely interconnect each screw and the fixation rod. Other anchoring devices include hooks and other types of bone screws Placement of pedicle screws in a percutaneous fashion has become desirable for all minimally invasive approaches to the spine. This technique generally relies heavily on a clear understanding of the local anatomy by the surgeon, as well as accurate radiographic guidance technology. Generally, placement is done using a large bore needle or a cannulated drill to start an initial hole for screw placement. Pedicle screws are preferably threaded in alignment with the pedicle axis and inserted along a trajectory that is determined prior to insertion of the screws. Misalignment of the pedicle screws during insertion can cause the screw body or its threads to break through the vertebral cortex and be in danger of striking surrounding nerve roots. A variety of undesirable symptoms can easily arise when the screws make contact with nerves after breaking outside the pedicle cortex, including dropped foot, neurological lesions, sensory deficits, or pain.

The placement of pedicle screws and other implants requires a high degree of accuracy and precision to ensure a proper trajectory for the implant. It is preferable that each instrument used in the process be inserted along the same trajectory to ensure proper placement. Known surgical procedures for inserting pedicle screws involve recognizing landmarks along the spinal column for purposes of locating optimal screw hole entry points, approximating screw hole trajectories, and estimating proper screw hole depth. Generally, large amounts of fluoroscopy are required to determine a proper pedicle screw trajectory and to monitor the advancement of a pedicle screws through the vertebra. However, prolonged radiation exposure to a patient and a surgeon is undesirable.

More technologically advanced systems such as the StealthStation™ Treatment Guidance System, the FluoroNav™ Virtual Fluoroscopy System (both available from Medtronic Sofamor Danek), and related systems, seek to overcome the need for surgeons to approximate landmarks, angles, and trajectories, by assisting the surgeons in determining proper tap hole starting points, trajectories, and depths. However, these systems are extremely expensive, require significant training, are cumbersome in operation, are difficult to maintain, and are not cost effective for many hospitals.

U.S. Pat. No. 6,725,080 describes an image-guided surgical navigation system including a tool guide that uses a trackable marker. The surgeon must manually position of the tool guide and maintain the position of the tool guide during surgery through the use of image guidance and computer software. Therefore, the position of the tool guide is subject to human error, fatigue and slippage, and requires continued operation of expensive equipment and prolonged exposure to radiation to maintain.

In another approach, a guidance system, such as a mini-robot, is mounted directly to the patient's bone. The system may require a larger surgical incision for anchoring the system to the bone and may require multiple incisions for multiple anchors, both of which increase tissue trauma to the patient.

One of the goals of Minimally Invasive Surgery MIS is to reduce trauma to the body. Reliably precise and accurate positioning of a tool trajectory allows reduction of the size of an access portal during surgery, thus, reducing tissue trauma.

A need exists for a system for guiding an implant that reduces human placement error, provides greater accuracy and precision in positioning tools and implants along a desired trajectory and maintains the desired trajectory during a surgical procedure. Further, a need exists for a guidance system with the aforementioned elements that is cost effective and does not require exposing a patient to prolonged radiation or additional tissue trauma.

SUMMARY OF THE INVENTION

Embodiments of the present invention provide a system and method for guiding an implant to an optimal placement within a patient. The system includes a trajectory guide for guiding and restricting instruments along a selected trajectory and a trajectory fixation device for fixing the trajectory guide in a selected position relative to the patient. A movable support mounts the trajectory guide and selectively moves the trajectory guide to align the trajectory guide with the selected trajectory prior to fixing the trajectory guide in the selected position. The moveable support is coarsely adjusted by hand. The guidance system incorporates a fine adjustment system, actuated either manually or using a servomotor, that provides accuracy and fine control in positioning of the trajectory guide. These embodiments provide a guidance system and method for implant placement that reduces human error, decreases some risks associated with surgery, and allows accurate and precise alignment with the desired trajectory. Increased accuracy and precision in tool alignment decrease the required size of access portals during surgery, which in turn, reduces trauma, and allows more effective implementation of MIS techniques. Additionally, the system is easy to use and cost effective.

According to a first aspect of the invention, a guidance system for use while inserting an implant is provided. The guidance system comprises a trajectory guide defining a path configured to align with a trajectory for guiding instruments along the trajectory and a lock for locking the trajectory guide in a selected orientation relative to a patient. The trajectory guide restricts the instruments to movement along the trajectory.

According to another aspect of the invention, a method for guiding an implant comprises the steps of determining a suitable trajectory for inserting the implant and fixing the trajectory relative to a patient using a trajectory guide. The trajectory guide is fixed at a fixation point located outside the body of the patient.

According to still another aspect, a method of inserting a pedicle screw into a pedicle bone of a patient is provided. The method comprises the steps of aligning a channel of a trajectory guide with a pedicle screw trajectory, locking the trajectory guide in an aligned position, inserting a first instrument through the trajectory guide to create a hole in the pedicle bone aligned with the pedicle screw trajectory, and inserting a pedicle screw through the trajectory guide and into the hole.

In yet another aspect of the invention, a surgical kit for inserting an implant is provided. The surgical kit comprises a first instrument for preparing a surgical site to receive the implant, a second instrument for inserting the implant in prepared surgical site and a trajectory guide for guiding said first instrument and second instrument along a trajectory. The first instrument and the second instrument are sized and configured to fit the trajectory guide.

According to another aspect of the invention, a guidance system for use while inserting an implant is provided. The guidance system includes a trajectory guide defining a path configured to align with a trajectory for guiding instruments along the trajectory and restricting the instrument to movement along the trajectory. The guidance system also includes a moveable support for moving the trajectory guide into a selected position and angular orientation. The moveable support is configured such that the position and angular orientation of the trajectory guide may be coarsely adjusted by hand. Additionally, the guidance system includes a fine adjustment system. The fine adjustment system is configured to align the trajectory guide with a desired location and angular orientation.

According to another aspect of the present invention, the trajectory guide may include a cannula. The guidance system may further include a lock for locking the trajectory guide in the desired orientation and location relative to a patient. The lock may include one of a set screw, a clamp, a collet, a friction lock, an electronic lock, a mechanical lock an electromechanical lock and a pneumatic lock. The moveable support may be configured such that the moveable support maintains a fixed location and orientation in the absence of additional external applied force when not locked down.

According to another aspect of the present invention, the fine adjustment system may be a manually actuated system. Further, the fine adjustment system may include at least one manually controlled linear micrometer. The fine adjustment system may include at least one manually controlled goniometer. According to a different aspect of the present invention, the fine adjustment system may be a servomotor system.

According to another aspect of the present invention, the fine adjustment system may be configured to move the trajectory guide in at least two perpendicular linear directions. Additionally, the fine adjustment system may be configured to move the trajectory guide through angles about two perpendicular rotation axes. The fine adjustment system may be configured to move the trajectory guide in at least one linear direction and through angles about at least one rotation axis.

According to an additional aspect of the present invention, the moveable support may be adapted to contact an anchor which is attached to a rigid portion of a patient body and wherein contact with the anchor stabilizes a location of the moveable support. The anchor may be a Steinman pin.

According to another aspect of the invention, a method for guiding an implant for a patient is provided. The method includes the step of determining a suitable trajectory including location and orientation for inserting the implant. The method also includes the step of manually moving a trajectory guide to near the suitable location and orientation using a coarse adjustment system. The method further includes the step of using one or more fine adjustment controls to move the trajectory guide from near the suitable location and orientation to the suitable location and orientation. Additionally the method includes the step of fixing the location and orientation relative to a patient using the trajectory guide. The trajectory guide is fixed at a fixation point outside the body of the patient. According to another aspect of the present invention, the method may further include the step of locking the coarse adjustment system after moving the trajectory to near the suitable location and orientation.

According to further aspects of the present invention the fine adjustment controls may be manually actuated. The fine adjustment controls may be actuated using one or more servomotors. The trajectory guide may include a cannula and the step of fixing the trajectory may include the steps of aligning a path through the cannula with the trajectory; and locking the cannula in an aligned position to lock the path into alignment with the trajectory. The method may also include the step of moving an instrument along the trajectory by inserting the instrument through the cannula. The method may further include the step of stabilizing the trajectory guide by contact with an anchor which is attached to a rigid portion of a patient body, after manually moving a trajectory guide to near the suitable location and orientation using a coarse adjustment system and prior to using one or more fine adjustment controls to move the trajectory guide from near the suitable location and orientation to the suitable location and orientation.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principals of the invention and, although not to scale, show relative dimensions.

FIGS. 10A-10H illustrate the pedicle region during the steps shown in FIG. 9.

DETAILED DESCRIPTION

Embodiments of the present invention provide an improved guidance system and method for guiding an implant, such as a pedicle screw, along a predetermined trajectory. The present invention will be described below relative to an illustrative embodiment. Those skilled in the art will appreciate that the present invention may be implemented in a number of different applications and embodiments and is not specifically limited in its application to the particular embodiments depicted herein.

The guidance system of an illustrative embodiment of the invention is used to insert a pedicle screw into a vertebra, though one skilled in the art will recognize that the invention can be used to place any suitable implant that requires a known trajectory. Examples of surgical procedures suitable for employing the guidance system of the present invention include, but are not limited to, insertion of interbody fusion devices, bone anchors, fixation devices, including rods, plates and cables, artificial disks and hip stems. The guidance system can be used to position any suitable implant, instrument and/or other device in any suitable procedure where guidance of the implant, instrument and/or device is key.

Figure 1:
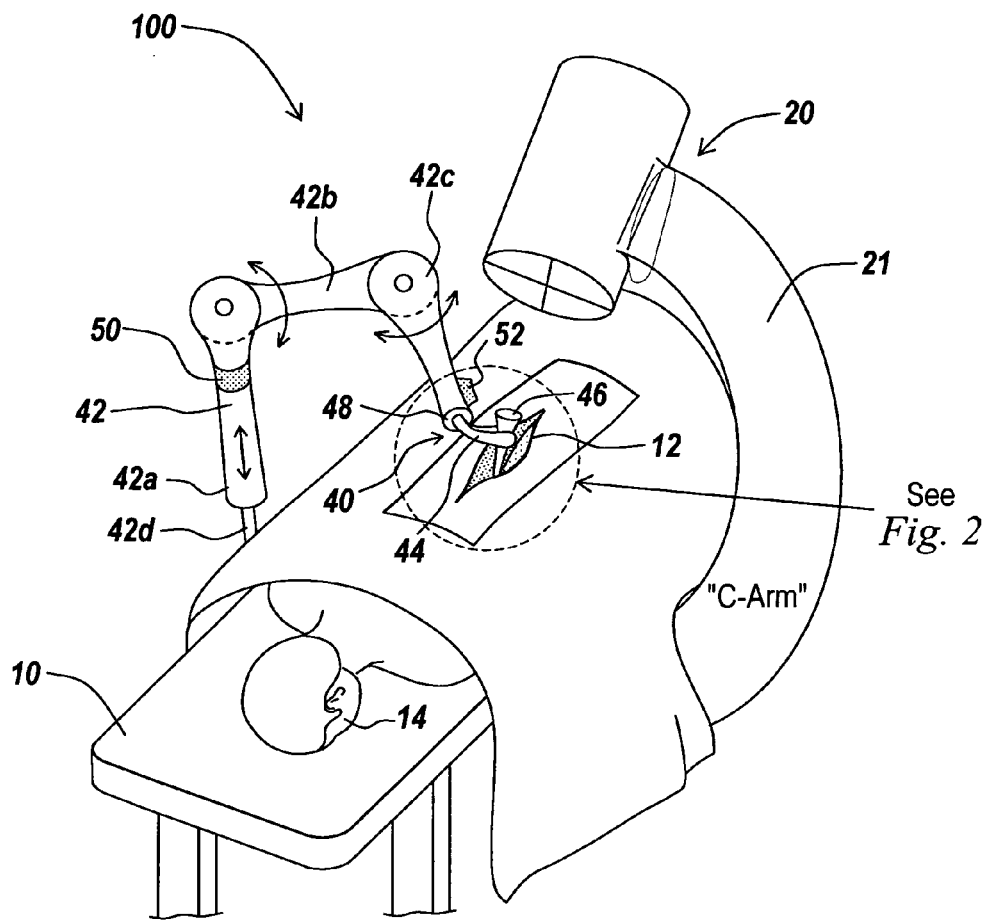
FIG. 1 illustrates a guidance system for guiding instruments used in a medical procedure according to an illustrative embodiment of the invention.

Referring to FIG. 1, a guidance system 100 of an illustrative embodiment of the invention facilitates placement of an implant, such as a pedicle screw, in a patient while minimizing radiation exposure. The guidance system 100 includes a trajectory guide 40 for guiding instruments used in performing a medical procedure into a surgical site along a selected trajectory and restricting the degree of motion of the instruments to movement along the selected trajectory. An imaging system 20, illustrated as a fluoroscopy unit 21, is provided for initially locating a suitable trajectory for the instruments used in performing a medical procedure, for example, instruments used to prepare an implant site and/or inserting an implant into the implant site. The system 100 may include an operating table 10 for positioning a patient 14 in a prone position to expose the surgical site 12 to the imaging system 20 and trajectory guide 40. As shown, the trajectory guide 40 is positioned outside of the patient's body.

Examples of instruments used to prepare an implant site and/or place an implant into a surgical site include, but are not limited to awls, bone taps, obturators, drills, guide wires and implants, such as screws, fusion devices, artificial disks and hip stems. One skilled in the art will recognize that the trajectory guide 40 is not limited to use with instruments used to prepare an implant site and/or place an implant into a surgical site and that the trajectory guide can be used to guide any suitable instrument used in a medical procedure along a selected trajectory.

The trajectory guide 40 can be any suitable device defining a path for guiding a surgical instrument, device and/or implant. The illustrative trajectory guide 40 includes a cannula 46 defining a path therethrough configured to align with the trajectory, though one skilled in the art will recognize that any suitable guide means may be used. The trajectory guide can have any suitable cross-section and is not limited to the cylindrical cross-section shown in the illustrative embodiments. The trajectory guide can be open or closed to define an open or closed path therethrough.

Figure 2:
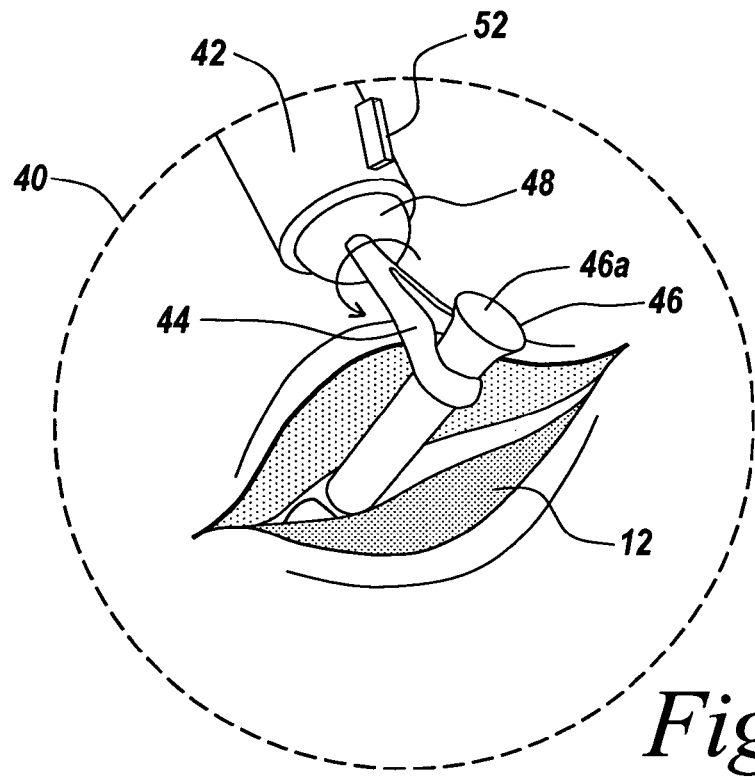
FIG. 2 is a detailed view of the trajectory guide of FIG. 1.

The cannula 46 can be spaced from or directly interface with the surgical site 12. The path through the cannula 46 forms a working channel configured to receive and guide selected surgical instruments along the longitudinal axis thereof. The cannula 46 preferably prevents the instruments from moving in any direction other than along the trajectory. The trajectory guide 40 further includes a movable guide support for moving the cannula 46 into a selected position relative to the patient in alignment with the trajectory and selectively locking the aligned cannula 46 in the selected position. The movable guide support includes a clamp 44 for holding the cannula 46 coupled to a distal end of a flexible arm 42 capable of selectively moving the clamp 44 in three dimensions to align the cannula 46 with a selected trajectory. A joint 48 may be provided for connecting the clamp 44 to the arm 42. FIG. 2 is a detailed view of the distal end of the trajectory guide 40 in the vicinity of the surgical opening 12 for the implant site on the patient. The flexible arm 42 allows the surgeon to bring the cannula 46 into the vicinity of the surgical site, while the joint 48 allows for fine-tuning of the orientation of the cannula 46.

The flexible arm 42 can comprise any suitable device for controlling the position and orientation of the trajectory guide 40 relative to the patient. As shown in FIG. 1, the flexible arm 42 comprises plurality of segments 42a, 42b, 42c pivotally connected together and mounted to a stand (not shown), the operating table 10, or other stable support. The first segment 42a is movably coupled to and slidable relative to a fixed shaft 42d though any suitable means, to allow the flexible arm to move along a vertical axis to raise or lower the flexible arm 42 relative to the operating table 10. The second segment 42b is pivotally coupled to the first segment 42a to provide a second degree of motion, while the third segment 42c is pivotally coupled to the second segment 42b to provide a third degree of motion. The clamp 44 and joint 48 cooperate to movably mount the cannula 46 or other suitable guide to the end of the third segment 42c. The use of a plurality of movably connected segments allows for the surgeon to move the cannula 46 in three dimensions. The flexible arm brings the trajectory guide into vicinity of an opening in the patient, while the joint 48 allows the surgeon to accurately position the cannula 46 at a selected angle relative to the patient.

Referring back to FIG. 2, according to an illustrative embodiment, the joint 48 is disposed at the distal end of the flexible arm 42 and comprises a ball joint having a wide degree of motion for orienting the cannula 46, though one skilled in the art will recognize that any suitable means for connecting the cannula to a movable support system may be used. The illustrative ball joint 48 provides a 160° cone of motion for positioning the cannula, though one skilled in the art will recognize that the ball joint 48 can have any suitable range of motion.

The clamp 44 extends from the ball joint 48 for holding the cannula in a selected position, as determined by the ball joint 48 and flexible arm 42. The clamp 44 can have any suitable size and configuration for rigidly holding the cannula 46 relative to the joint 48. The clamp 44 allows for the position of the trajectory to be fixed at a fixation point outside the body, rather than securing the trajectory guide at a location within the body by, for example, securing the trajectory guide to a body part. The use of an external fixation point facilitates positioning of the trajectory guide by the surgeon, while reducing the risk of infection to the patient.

The guidance system 100 further includes a least one cannula lock for locking the trajectory guide in a selected orientation relative to the patient. After a surgeon positions the cannula 46 in a selected orientation, such that a path through the cannula aligns with a previously determined trajectory, a lock or a series of locks associated with the movable guide support fixes the position of the cannula 46 to lock the trajectory. For example, the cannula lock can include at least one arm lock 50 and a joint lock 52. The arm lock 50, which can comprise a plurality of locks, each associated with an interface between two segments of the flexible arm 42, locks the flexible arm 42 in a selected position to secure the segments 42a, 42b, 42c, 42d relative to each other. The joint lock 52, when actuated, locks the joint 48 to the distal end of the third segment 42c to fix the cannula 46 relative to the flexible arm 42. The surgeon can manually actuate the cannula lock or automatically actuate the cannula lock to fix the position of the cannula 46 relative to the surgical site through any suitable means.

The locking mechanisms for the arm lock 50 and the joint lock 52 can comprise any suitable locking mechanism known in the art. Examples of suitable types of locking mechanisms include pneumatic locks, mechanical locks, such as set screws, clamps, collets and friction locks, electronic locks, magnetic locks, electromechanical locks, such as electromechanical locks utilizing a solenoid mechanism, and others known in the art.

Figure 3:
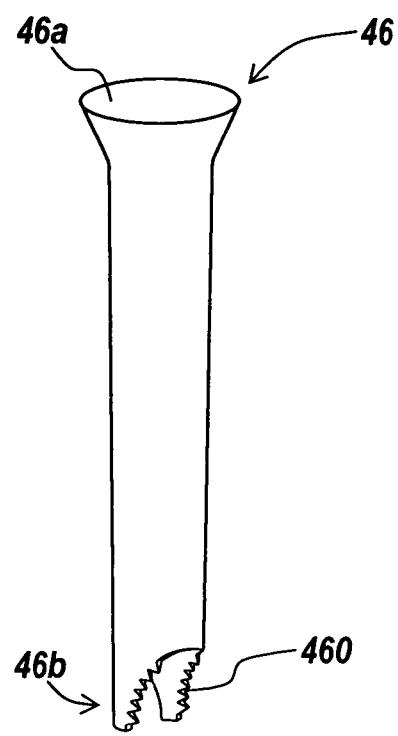
FIG. 3 is a side view of a cannula used in the trajectory guide of FIGS. 1 and 2.

FIG. 3 is a side view of an embodiment of a cannula 46 for guiding instruments according to an embodiment of the invention. In the embodiment shown in FIGS. 1 and 2, the cannula 46 comprises a hollow tubular body suitable for insertion in and/or placement adjacent to a patient's body. The cannula 46 has at least one hollow channel or lumen defining a path extending from an open first end 46a of the cannula 46 to an open second end 46b of the cannula 46b. The cannula 46 can be formed of any suitable surgical material, such as, but not limited to, surgical stainless steel.

The tubular body 46 can be rigid, semi-rigid or flexible, and can have any suitable size, shape and configuration suitable for defining a trajectory for implant placement. In the illustrative embodiment, the cannula 46 is straight to define a straight trajectory. Alternatively, the cannula 46 can be curved or have any other suitable shape to define a curved or otherwise shaped trajectory. The cannula 46 is not limited to a tubular structure having closed sidewalls and can be any component that defines a path, including an open channel or a solid member.

As shown in FIG. 3, the second end 46b of the cannula 46 can be configured to interface with bone or another feature to facilitate positioning of the cannula 46 along a suitable trajectory relative to the surgical site. As shown, the cannula 46 can include teeth 460 formed on an outer surface of the lower end for engaging the pedicle bone.

The cannula 46 can have any suitable diameter suitable for guiding an instrument along a path defined by the cannula. According to one embodiment, the cannula 46 can be configured to receive an instrument within the channel. In this embodiment, the inner diameter of the cannula 46 is slightly larger than the outer diameter of the instrument guided by the cannula, so that the instrument can be inserted through the cannula while the side walls of the cannula maintain the instrument at a predetermined angle relative to the patient. Alternatively, an instrument to be guided by the cannula is configured to slide over the cannula 46, with the cannula 46 maintaining the orientation of the instrument as the instrument slides relative to the cannula. In this embodiment, the cannula 46 can have an outer diameter that is slightly less than an inner diameter of an instrument. One skilled in the art will recognize that the cannula 46 can have any suitable size and configuration for guiding an instrument along a selected trajectory.

In one embodiment, the cannula 46 includes one or more stops (not shown) for limiting the insertion depth of an instrument guided through the cannula 46. Each stop is configured to abut a corresponding protrusion or other feature on the instrument to prevent the instrument from moving past the stop, thereby limiting the insertion depth of the instrument.

Figure 4A:
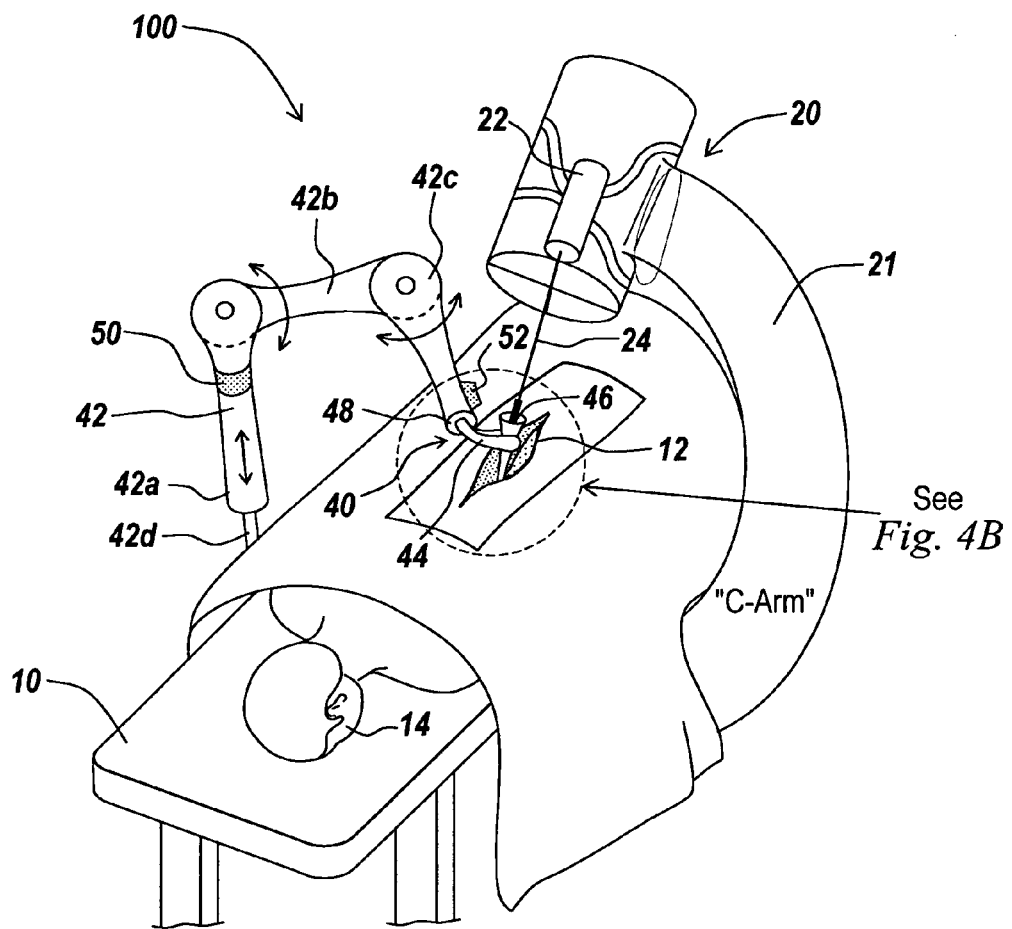
FIG. 4A illustrates a guidance system including a laser unit to assist in identifying a suitable trajectory according to an embodiment of the invention.
Figure 4B:
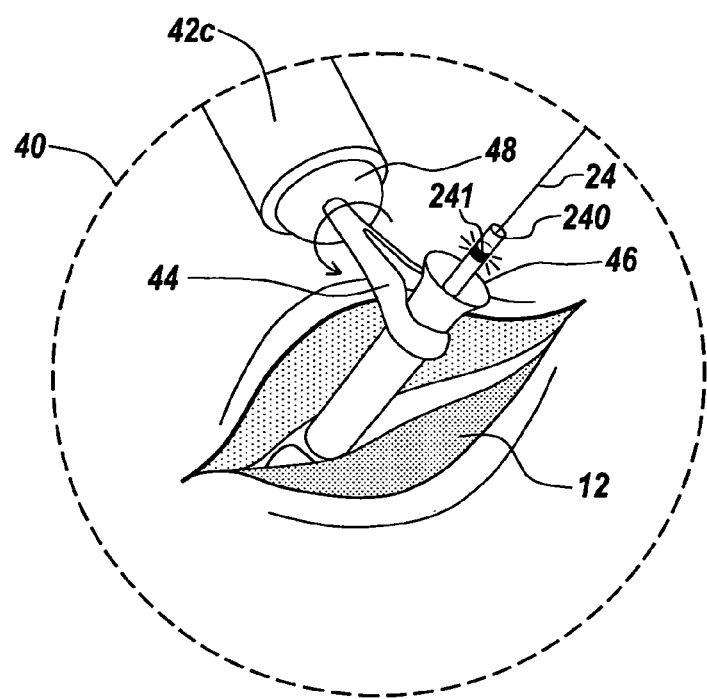
FIG. 4B is a detailed view of the trajectory guide of the system of FIG. 4A.

The imaging system 20 can comprise any suitable means for identifying a suitable trajectory for surgery and is not limited to a fluoroscopy unit 21. According to one embodiment, shown in FIGS. 4A and 4B, the fluoroscopy unit 21 can include a laser unit 22 for producing a light beam 24, for example, a focused light beam, for marking the trajectory after the fluoroscopy unit 21 identifies a suitable trajectory. As shown in FIG. 4B, the light beam 24 aligns with and extends through the cannula 46 when the cannula channel aligns with the trajectory. An orientation marker 240, configured to be inserted in the cannula 46, facilitates alignment of the light beam 24 with the path through the cannula 46. The orientation marker 240 can include one or more radiopaque portions 241, visible using fluoroscopy, to facilitate alignment.

According to the illustrative embodiment, the laser unit 22 for marking a trajectory comprises a Dual Radiation Targeting System (DRTS™) Platform system available from Min-Rad, Inc. of Buffalo, N.Y. Suitable systems for using a laser to identify a trajectory are described in U.S. Pat. Nos. 6,096,049, 5,810,841, 5,644,616 and 5,212,720, which are herein incorporated by reference in their entirety.

One skilled in the art will recognize that any suitable light source may be used to produce the light beam 23 and that the invention is not limited to a laser unit. For example, the imaging system 20 can employ an infrared light source, an incandescent light source or any suitable light source capable of producing a light beam marking a trajectory.

Figure 5A:
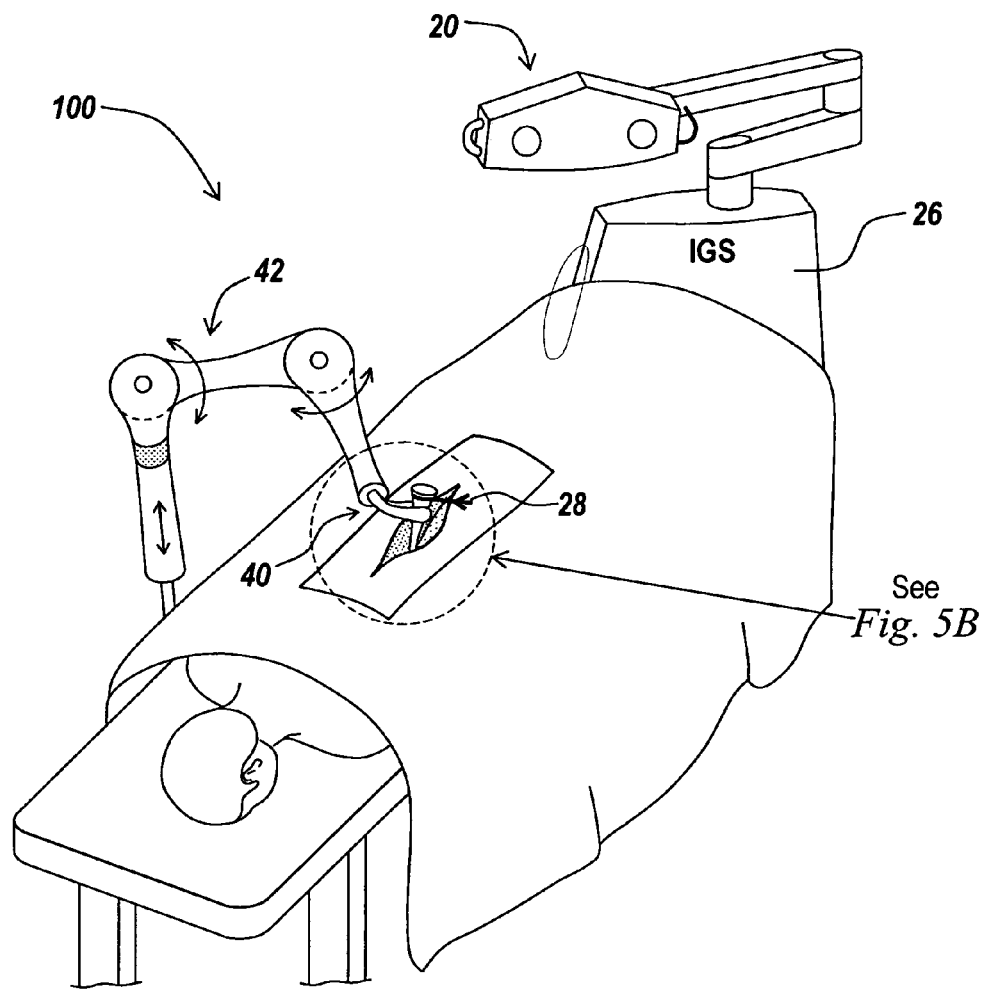
FIG. 5A illustrates a guidance system including an image guided surgery unit to assist in identifying a suitable trajectory according to an embodiment of the invention.
Figure 5B:
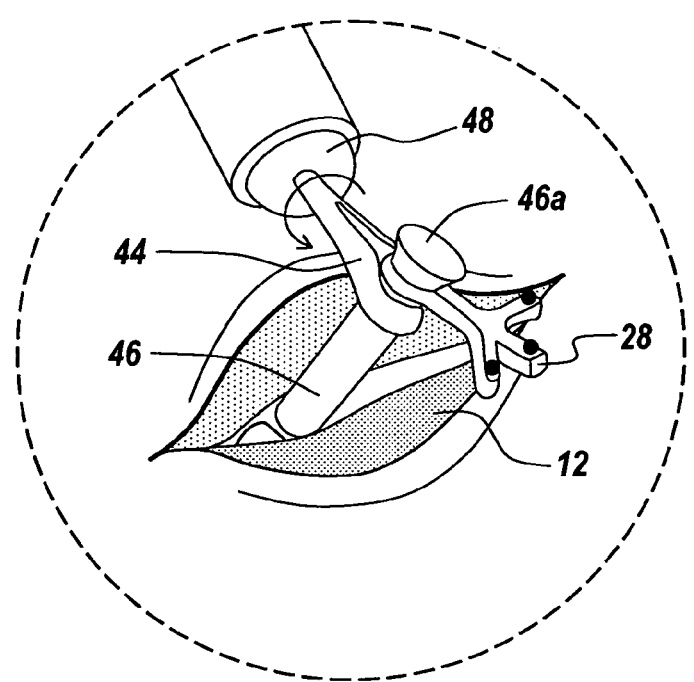
FIG. 5B is a detailed view of the trajectory guide of the system of FIG. 5A.

In another embodiment of the invention, as shown in FIGS. 5A and 5B, the imaging system 20 comprises an image-guided surgery unit 26. As shown in FIG. 5B, the guidance system 100 can include a 3-D array reference 28 to facilitate identification of a suitable trajectory. The 3-D array reference 28 is coupled to a proximal end 46a of the cannula 46 and cooperates with the image-guided surgery unit 26 to identify a suitable trajectory for implant placement and align the cannula 46 with the trajectory.

In one embodiment, the imaging system 20 employs the VectorVision® navigation system by BrainLab AG of Heimstetten Germany, which provides simultaneous navigation in CT and fluoroscopic images during surgery.

Figure 6A:
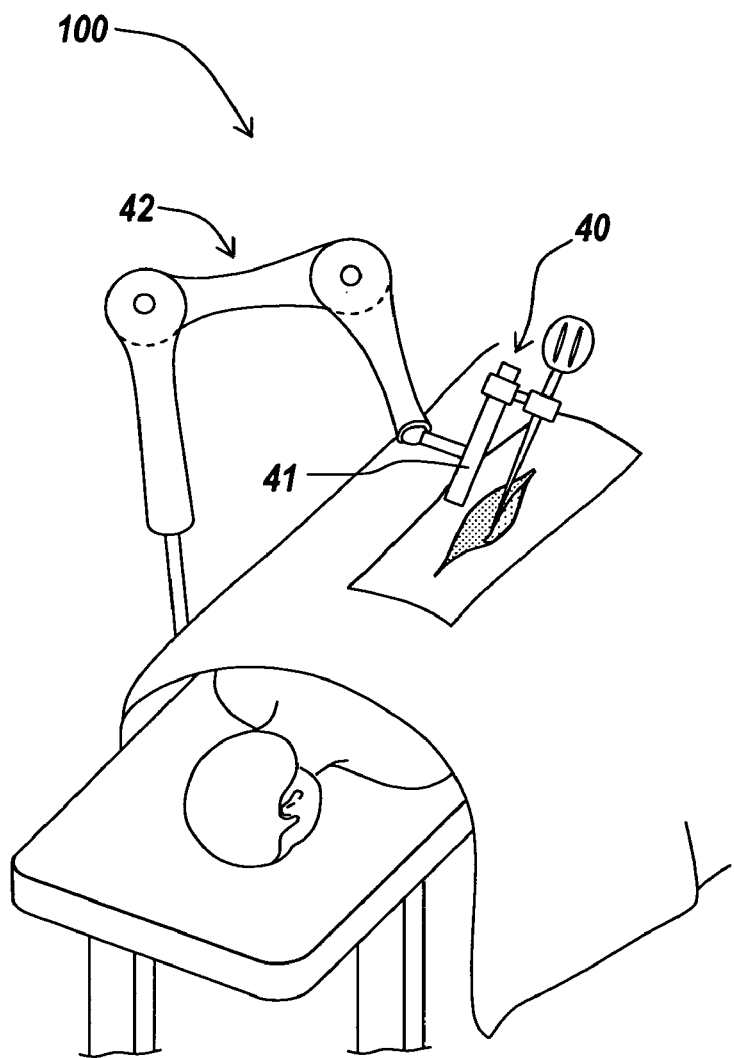
FIG. 6A illustrates a guidance system having a trajectory guide including a track according to an embodiment of the invention.
Figure 6B:
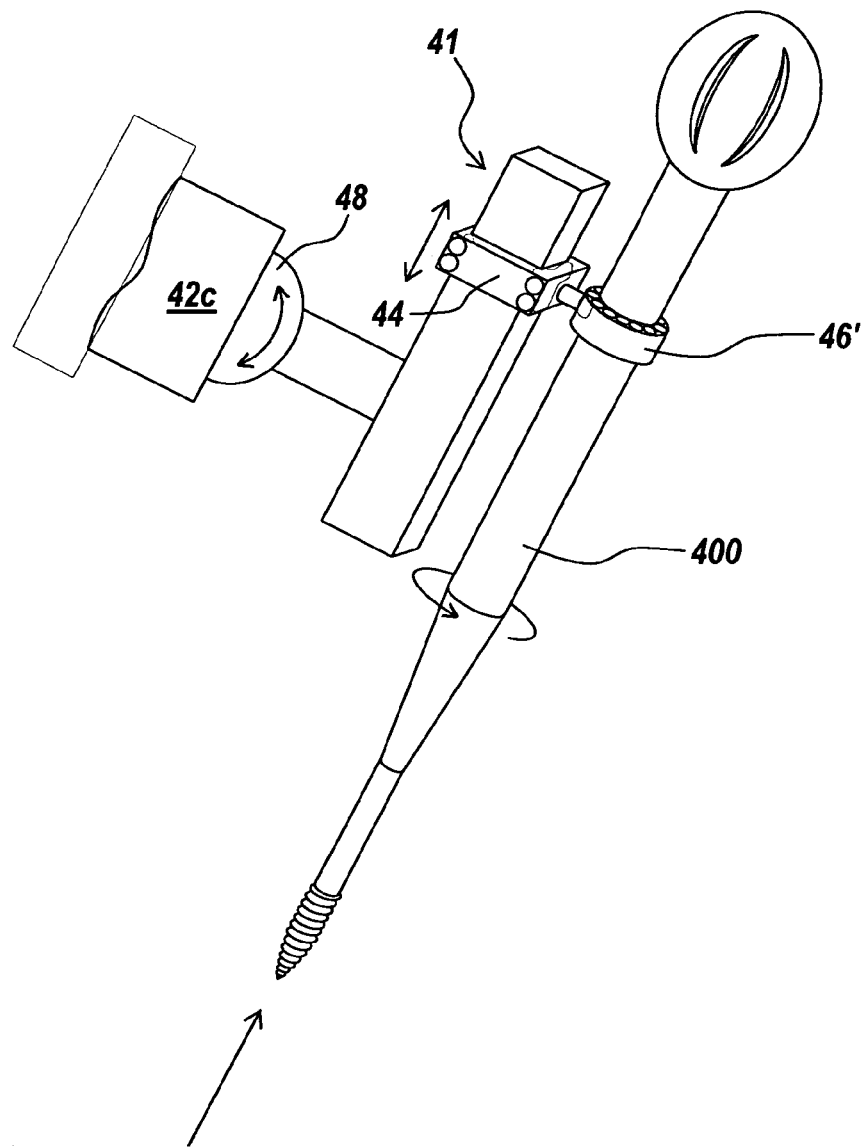
FIG. 6B is a detailed view of the trajectory guide of FIG. 6A.

According to one embodiment of the invention, as shown in FIGS. 6A and 6B, the trajectory guide 40 can include a track 41 configured to receive a clamp 44' connected to a cannula or an annular ring 46' defining the path for the instruments. In the embodiment shown in FIGS. 6A and 6B, the annular ring 46' holds a screw driver 400 in alignment with a selected trajectory. The annular ring 46' traverses the track 41, which allows the annular ring 46' to move along the trajectory after the trajectory guide fixes the trajectory by fixing the track 41 in a selected orientation. The user can move the instrument along the trajectory towards or away from pedicle, while the track maintains angular and spatial orientation of the instrument. The annular ring 46' and track 41 can allow instruments inserted therein to rotate on a fixed axis, facilitating insertion of an implant along the trajectory. One skilled in the art will recognize that any suitable means for moving the trajectory guide 40 along the trajectory may be used.

Figure 7:
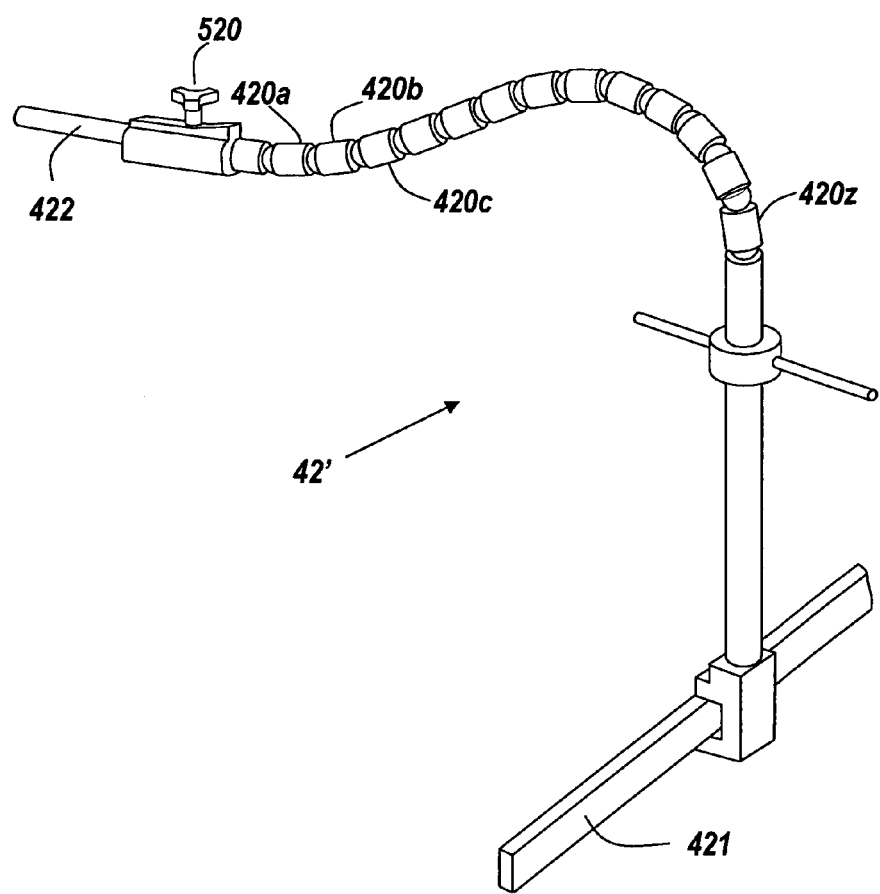
FIG. 7 illustrates a flexible arm suitable for use with the guidance system of FIG. 1 according to another embodiment of the invention.

FIG. 7 illustrates another embodiment of a flexible arm 42' suitable for use in the guidance system 100 of the present invention. The flexible arm 42' includes a plurality of movably linked segments 420a, 420b . . . 420z and a base 421 attached to the operating table. The flexible arm 42' includes a lock, illustrated as a three-lobed knob 520 located between the series 420 of linked segments and a joint segment 422, for locking the arm 42' and associated trajectory guide 40 in a selected position and orientation. The illustrative arm 42' "locks" down the series of linked segments 420 and the joint segment 422 when the knob 520 is turned clockwise. As the user turns the knob, the knob applies a force to rods located within the series of linked segments and the joint segment 422 to create an interference or friction fit at the joint between the series of linked segments and the joint segment 422. As the knob turns, the joint located at the knob is clamped tight by creating a high degree of friction between the two pieces. These friction fits immobilize all the linked segments to create a rigid arm. Turning the knob counter clockwise releases pressure induced on all the surfaces allowing the arm to become "flexible" again.

The flexible arm 42' illustrated in FIG. 7 is available from Mediflex® Surgical Products of Islandia, N.Y., though one skilled in the art will recognize that the flexible arm can have any suitable configuration, size and source.

Figure 8:
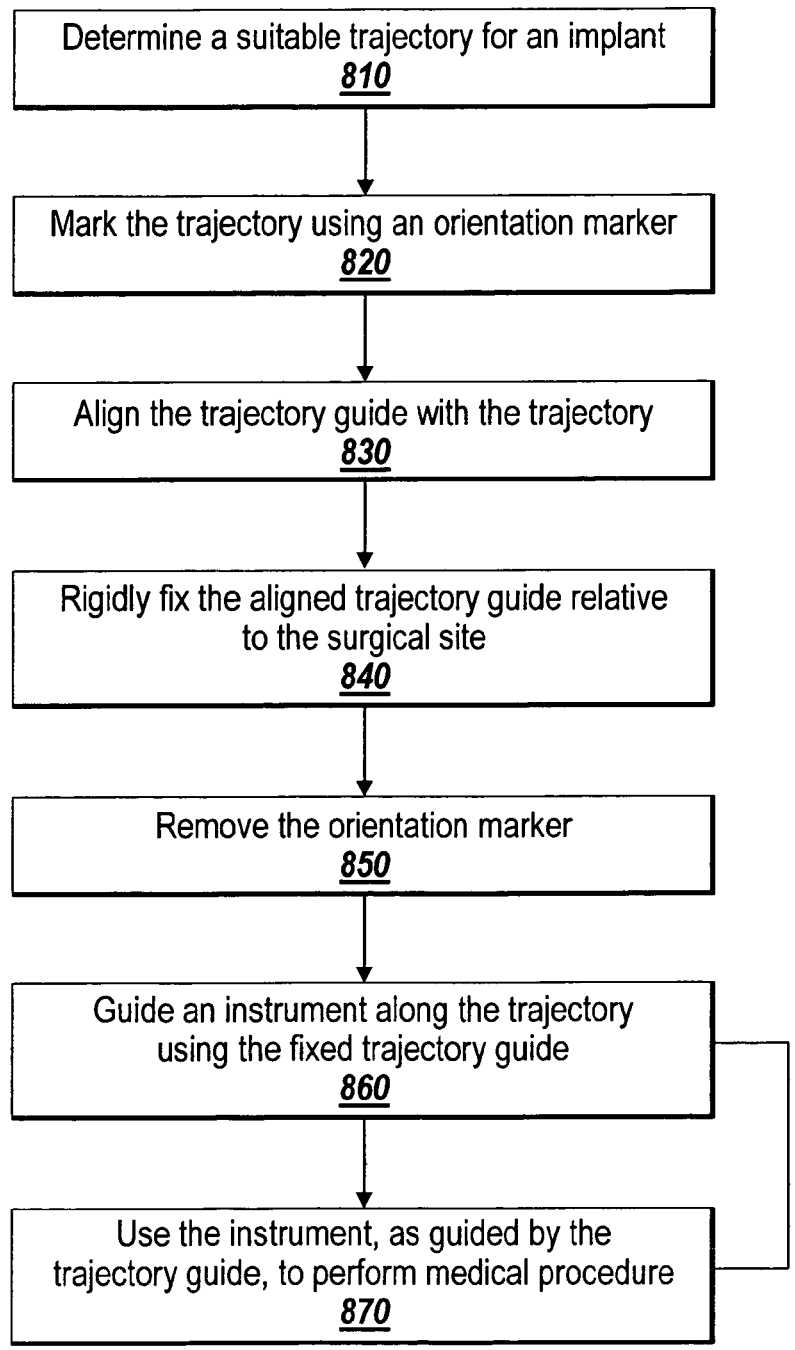
FIG. 8 is a flow chart diagramming the steps involved in using the guidance system of FIG. 1 to guide instruments and implants into a selected surgical site along a suitable trajectory.

FIG. 8 is a flow chart diagramming the steps involved in using the guidance system 100 of FIG. 1 to guide instruments and implants into a selected surgical site along a suitable trajectory with minimal radiation exposure. The illustrative guidance system 100 and method provide reproducible, simplified steps for accurately placing an implant in a patient.

In step 810, a surgeon first determines a suitable trajectory for an implant. The step of determining a trajectory involves identifying a potential orientation, i.e., the location and angle, of a surgical implant site, such as a pedicle, using any suitable technique. Examples of suitable techniques for determining a suitable trajectory include using a k-wire, fluoroscopy, MRI, laser navigation and image guided surgery. For example, a surgeon generally identifies a trajectory by placing a patient on the operating table 10 in a selected position, locating anatomical landmarks on the patient, for example, using fluoroscopy, and locating a suitable incision site over the disc space of the patient. One skilled in the art will recognize that any suitable device and/or method for determining a suitable trajectory may be used.

After determining a suitable trajectory in step 810, the surgeon can mark the trajectory using an orientation marker in step 820. Examples of suitable orientation markers include, but are not limited to, a laser, a needle, an awl and an obturator.

After marking the orientation, the surgeon aligns the trajectory guide 40 with the trajectory in step 830. According to the illustrative embodiment, the surgeon aligns the trajectory guide by first bringing the cannula 46 into the vicinity of the surgical site and the trajectory to the surgical site by moving the flexible arm 42 along one or more suitable axes. The user then moves the cannula relative to the flexible arm 42 until a path through the cannula 46 aligns with the trajectory and the cannula 46 defines the trajectory. In this step, the surgeon uses the orientation marker as a guide for alignment of the trajectory guide path with the trajectory defined in step 810. For example, the surgeon can place the cannula over the orientation marker to align the cannula with the trajectory.

After alignment, the surgeon rigidly fixes the aligned trajectory guide in the selected position, orientation and angle relative to the surgical site in step 840 so as to define a fixed, guided trajectory for the instruments used in inserting instruments for the implant and the implant itself.

After fixing the trajectory, the surgeon removes the orientation marker in step 850, leaving the trajectory guide in the selected position aligned with the trajectory.

In step 860, the surgeon guides an instrument along the trajectory using the fixed trajectory guide. The use of a fixed trajectory guide defining the trajectory allows the surgeon to guide the instruments along the specified trajectory without requiring fluoroscopy. In step 870, the user uses the instrument, as guided by the trajectory guide, to perform medical procedure, for example, to prepare the surgical site and/or to insert the implant along the trajectory. The user can repeat steps 860 and 870 using different instruments as necessary to perform the selected medical procedure. The trajectory guide, which remains fixed, ensures that each instrument travels along the same trajectory.

Figure 9:
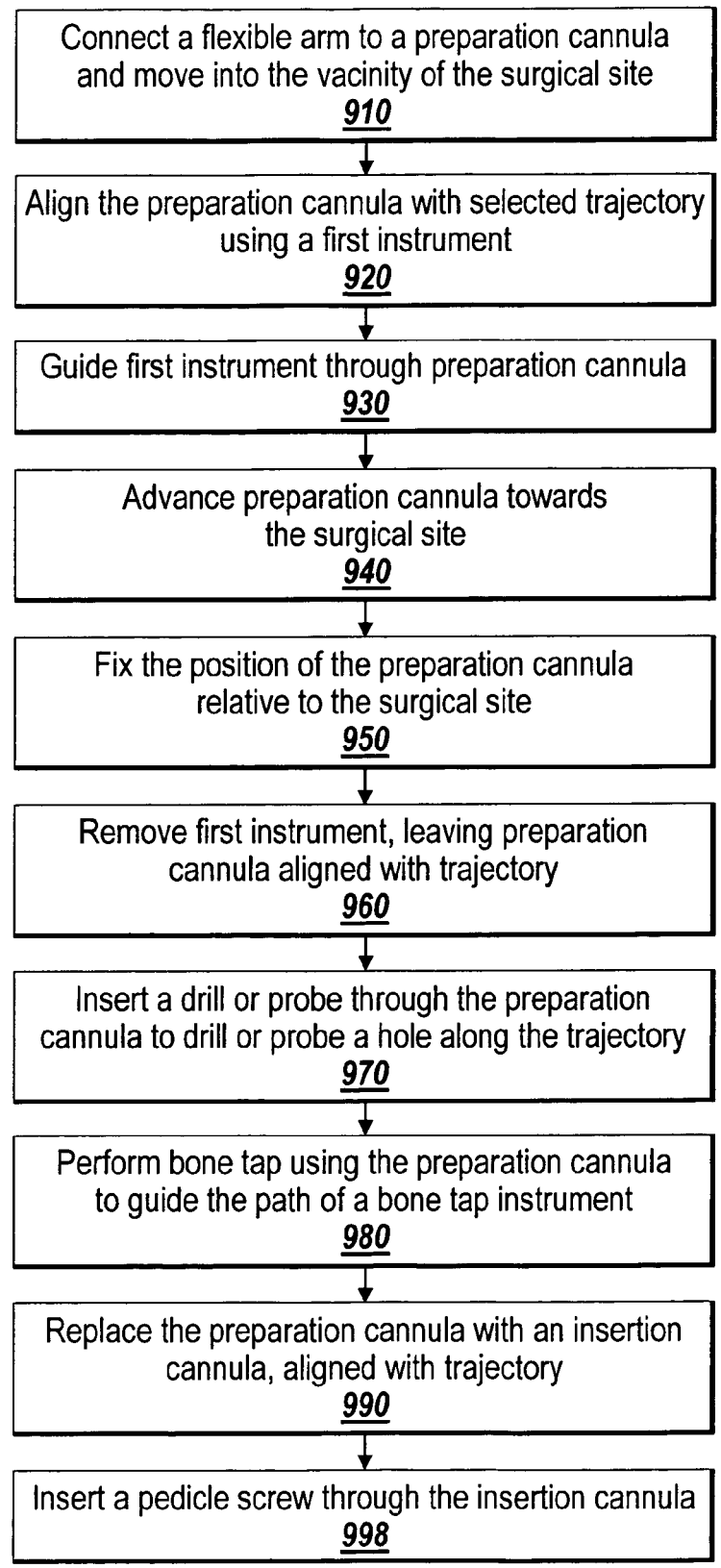
FIG. 9 is a flow chart diagramming the steps involved in using the guidance system of FIG. 1 to prepare a pedicle and insert a pedicle screw along a trajectory.

FIG. 9 illustrates the steps involved in preparing a pedicle and inserting a pedicle screw into the prepared pedicle using the guidance system 100 of the illustrative embodiment of the invention. The illustrative method ensures proper pedicle screw placement with minimal radiation exposure. FIGS. 10A-10H illustrate the surgical site during each of the respective steps of FIG. 9. As shown, throughout the process, a trajectory guide maintains a trajectory T-T for guiding the pedicle instruments and the pedicle screw into the surgical site.

After identifying a suitable trajectory and marking the trajectory using a laser beam that extends from the incision point of the patient, the surgeon, in step 910, connects a flexible arm 42 to a preparation cannula 46 via a clamp 44 and moves the assembly into the vicinity of the surgical site 12, as shown in FIG. 10A. The preparation cannula 46 guides instruments used to prepare the pedicle 120 for receiving a pedicle screw. Preferably, the incision point for a pedicle screw trajectory is at the junction of the pars interarticularis, the superior articular facet and the transverse process, though one skilled in the art will recognize that any suitable location can be used as the incision point.

In step 920, the surgeon aligns the cannula 46 with the trajectory using a first instrument. The surgeon aligns the cannula 46 by guiding an obturator/awl 82 through the cannula 46 to the incision point, such that the tip 82a of the instrument touches the laser dot produced by the laser at the incision point. Then, the surgeon aligns the cannula 46 with the laser beam. As shown in FIG. 10B, the illustrative obturator/awl 82 includes a pointed tip 82a suitable for punching through the cortical wall of the patient to create a path, aligned with the trajectory, down the muscle plane to the facet. Alternatively, the surgeon inserts the obturator/awl 82 prior to moving the assembly towards the surgical site, then aligns the cannula using the point 82a of the obturator/awl 82.

In step 930, the surgeon continues to guide the first instrument, illustrated as the obturator/awl 82, through the aligned cannula until the tip 82a punches through cortical wall to begin the incision.

In step 940, while maintaining the obturator/awl 82 in alignment with the laser, the surgeon advances the cannula 46 over the obturator/awl 82 towards the surgical site, as shown in FIG. 10C. In the illustrative embodiment, the surgeon advances the cannula until the teeth 460 formed on the distal end of the cannula engage the vertebral facet.

Alternatively, the surgeon first punches through the cortical wall using the obturator/awl separate from the cannula 46, aligns the obturator with the trajectory using the laser and slides the cannula 46 over the aligned obturator to align the cannula 46 and create the initial incision at the surgical site.

After assuring that the cannula 46 is still aligned with the laser and making proper adjustments, if necessary, the surgeon locks the flexible arm 42 to fix the position of the cannula 46 relative to the surgical site in step 950.

In step 960, the surgeon removes the obturator/awl 82, leaving the cannula 46 in the selected orientation, as shown in FIG. 10D.

In an optional step 970, the surgeon inserts a drill or probe through the cannula 46 to drill or probe a hole along the trajectory through the center of the pedicle. The drill or probe is sized and configured to fit the path defined through the cannula 46, and advance along the trajectory, guided by the cannula. The close fit between the cannula and the instrument prevents the instrument from deviating from the trajectory.

Figure 10E:
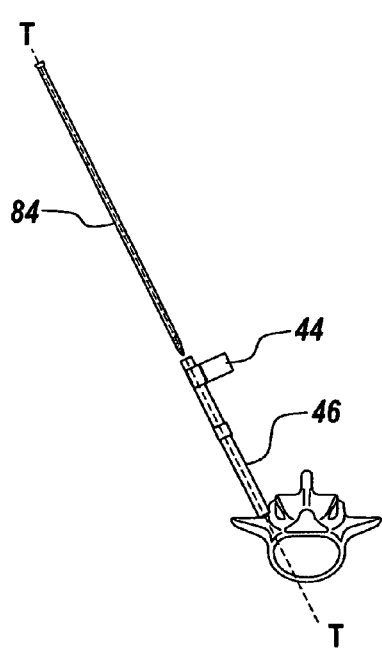

In step 980, the surgeon performs a bone tap using the cannula 46 to guide the path of the bone tap instrument used to perform the bone tap. To perform the bone tap, the surgeon inserts a bone tap 84 through the cannula 46, as shown in FIG. 10E, taps the pedicle and removes the tap from the cannula. During the bone tap, the cannula 46 constrains the motion of the bone tap 84 along the trajectory, preventing the bone tap from removing bone that outside of the trajectory.

Figure 10F:
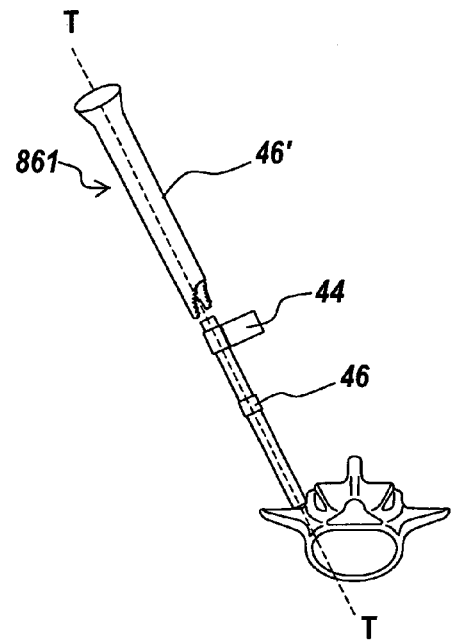
Figure 10G:
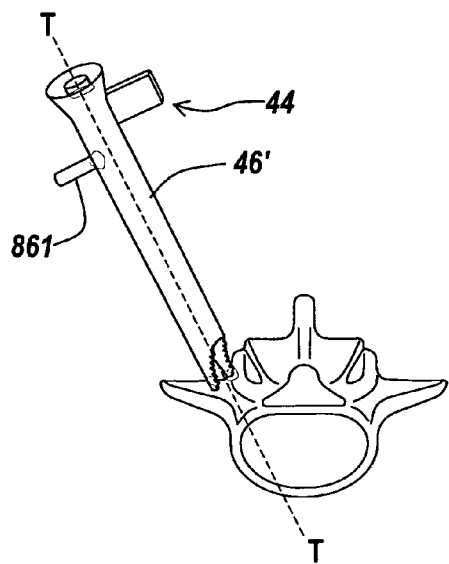
Figure 10H:
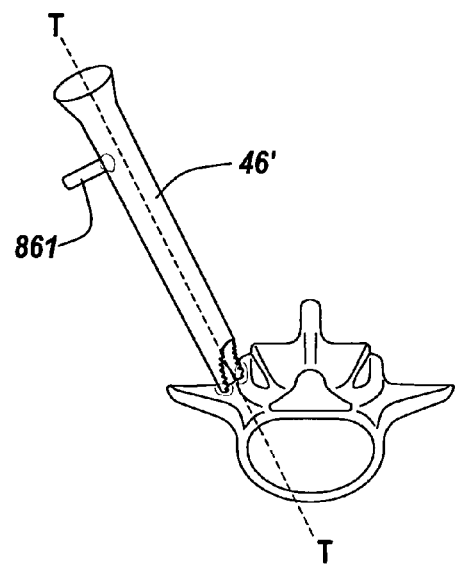

In step 990, the surgeon replaces the preparation cannula 46 with a larger insertion cannula used to insert a pedicle screw along the trajectory while holding back the tissue in the vicinity of the insertion site. As shown in FIGS. 10F-10H, the surgeon replaces the cannula 46 by sliding the C-shaped insertion cannula 46' over the cannula 46, as shown in FIG. 10F, and securing insertion cannula teeth 862 to the transverse process, as shown in FIG. 10G. While the cannula 46 maintains the position of the insertion cannula 46' in alignment with the trajectory, the user detaches the cannula 46 from the clamp 44 and attaches the clamp 44 to an attachment site 861 on the insertion cannula 46'. If necessary, the surgeon recalibrates the trajectory. Then, the user removes the cannula 46, leaving the insertion cannula 46' defining the trajectory T-T, as shown in FIG. 10H.

The insertion cannula 46' has a larger diameter than the cannula 46, suitable for dilating and retracting the tissue in the vicinity of the insertion site, which further opens and exposes the surgical site to facilitate insertion of a pedicle screw.

Finally, in step 998, surgeon inserts a pedicle screw through the insertion cannula 46', as shown in FIG. 10H, such that the pedicle screw aligns with the trajectory. The surgeon inserts the pedicle screw by inserting the stem of a pedicle screw through the incision site made in step 930 and into the hole defined by the bone tap in step 980. Using a screwdriver inserted through the insertion cannula 46', the surgeon then secures the pedicle screw to the pedicle.

According to an alternate embodiment, the preparation cannula 46 is used to both prepare the pedicle and insert the pedicle screw without using a tissue retractor.

The guidance system 100 can include a single uniformly sized cannula sized and dimensioned to receive and guide all instruments used in preparing a pedicle and inserting a screw into the pedicle along a trajectory. For example, all instruments used in the preparation and insertion process can have an outer diameter approximately equal to the inner diameter of the cannula. Alternatively, the guidance system 100 can include a plurality of cannulas, each sized and dimensioned to receive and guide a selected subset of instruments. For example, a first cannula, i.e., a pedicle preparation cannula, can be sized and configured to receive and guide a first subset of instruments used in the pedicle preparation process, such as the probe, drill and tap. A second cannula, i.e., a screw insertion cannula, can be sized and dimensioned to receive and guide a second subset of instruments, for example, the screw driver, used to insert a screw into the pedicle. In another embodiment, a guidance system includes only a pedicle prep cannula, allowing the surgeon to subsequently insert the screw without guidance.

According to another embodiment of the invention, the process of preparing for and inserting a pedicel screw can omit the step of tapping the bone in step 980 when the cannula 46 is used to insert self-tapping pedicle screws. In this embodiment, the surgeon defines a suitable trajectory, aligns the cannula with the trajectory and secures the cannula 46 in a fixed orientation in alignment with the trajectory, as described above. Then, the surgeon inserts a self-tapping screw along the trajectory under the guidance of the cannula 46 sized and shaped to receive and guide a screwdriver for screwing the self-tapping screw in place.

Those skilled in the art should recognize that there are many different types of cannulas and many different ways in which cannulas could be used. For example, a cannula could be rigid, semi-rigid, or flexible and could be configured in any number of different forms, such as a catheter, needle, endoscope, implement inserter, etc.

The use of a rigid lock for locking a trajectory guide into a selected position aligned with a suitable trajectory provides significant advantages over prior systems and methods for guiding instruments during a medical procedure. By maintaining the trajectory guide position with a rigid arm, image guidance is not required and therefore, the guide system does not require the continued use of a tracking marker after initial alignment of the trajectory guide with the cannula. Once the trajectory has been determined, the tracking marker is no longer used while guiding instruments to the working space. The use of a rigidly fixed cannula further eliminates the need for guide wires to maintain a selected trajectory, which tend to advance in the patient, causing injury, and are not as accurate.

Figure 11:
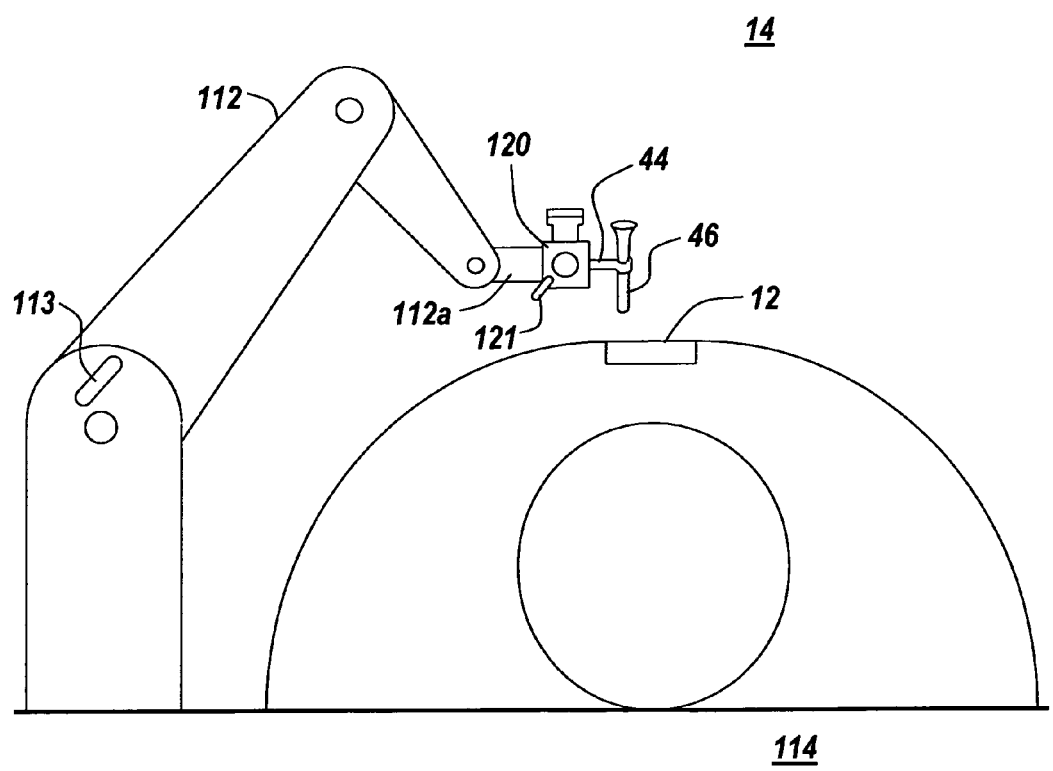
FIG. 11 illustrates a guidance system including a manual fine adjustment system according to another illustrative embodiment of the invention.

FIG. 11 illustrates another illustrative embodiment of the present invention that incorporates a manual fine adjustment system. In this embodiment, a moveable support 112 is attached to a stable structure 114 external to the patient. The support may be clamped, glued, bolted or attached to the stable structure 114 in any other manner that would prevent attachment points from moving after the support has been positioned and attached to the stable structure 114. The moveable support 112 is configured to be moved by hand such that the cannula 46 can be positioned near a desired location and orientation. The moveable support 112 incorporates all of the features of the flexible arm 42 described previously and includes additional features that will be detailed below. A fine adjustment system 120 is attached to the distal end of the moveable support 112a. The fine adjustment system 120 allows the cannula 46 to be easily positioned precisely and accurately. A clamp 44 attached to the fine adjustment system 120 is used to hold the cannula 46.

The moveable support 112 can incorporate a moveable support lock 113. Although this embodiment uses one moveable support lock 113, any number of moveable support locks may be used. The movable support 112 may be comprised of a plurality of segments. Once the moveable support is positioned manually, the moveable support lock 113 is used to lock all of the segments in position relative to each other. To assist in the placement and positioning of the moveable support 112, drag can be built into the moveable support 112. The drag would temporarily hold all of the segments in the desired location until the moveable support can be locked. This would allow the surgeon to place the guidance system by hand, remove his/her hands and then lock down the moveable support 112 without the moveable support shifting position.

Figure 12A:
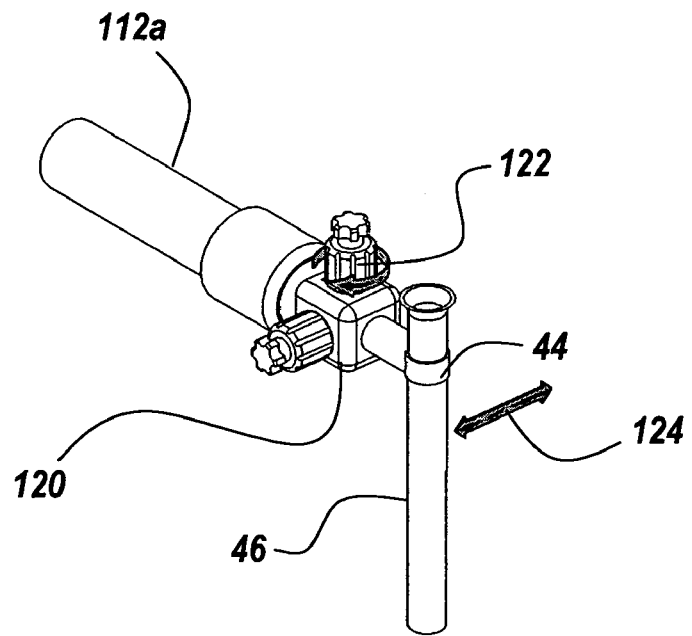
FIG. 12A is a detailed view of the guidance system of FIG. 11 illustrating linear fine adjustment in the x-direction.
Figure 12B:
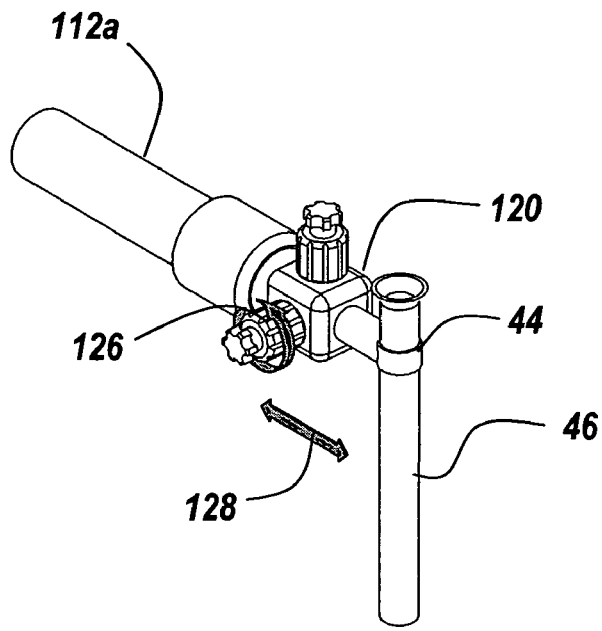
FIG. 12B is a detailed view of the guidance system of FIG. 11 illustrating linear fine adjustment in the y-direction.

FIGS. 12A and 12B show detailed views of the illustrative embodiment of the guidance system with a manual linear fine adjustment system. FIG. 12A illustrates fine adjustment in the x-direction 124. The fine adjustment system 120 is attached to the distal end of the moveable support 112a. In this particular embodiment, the fine adjustment system 120 is configured to translate the clamp 44 and the cannula 46 in two perpendicular linear directions. Rotation of the x-fine adjustment control 122 knob results in the clamp 44 and the cannula 46 translating in the x-direction 124. FIG. 12B illustrates fine adjustment in the y-direction 128. Rotation of the y-fine adjustment control 126 knob results in translation of the clamp 44 and the cannula 46 in the y-direction. The fine adjustment control knob 122 and 126 are connected to a gearing mechanism which converts the rotational motion into linear motion. The particular linear translation mechanism is chosen based on many factors including total travel range and desired accuracy. For example, one micrometer translation mechanism can translate with a precision of 0.00008 cm over 1 cm of travel with a 5 cm maximum travel distance. An extended length version of the micrometer translation mechanism can translate with the same accuracy over a 30 cm travel distance. In general, the greater the maximum travel distance, the lower the precision of the translation mechanism. The translation drive mechanism may be a graduated micrometer, a digital micrometer, a fine screw, a differential screw or any other manual drive mechanism that provides sufficient accuracy, precision and maximum range. For example, a digital micrometer translator can accurately measure a 0.0001 cm change in linear position.

Figure 13A:
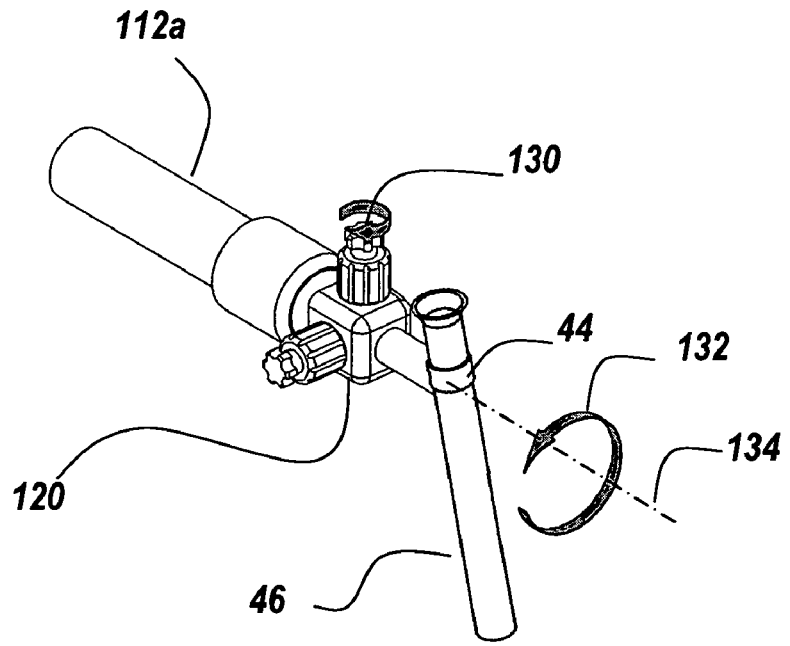
FIG. 13A is a detailed view of the guidance system of FIG. 11 illustrating angular fine adjustment about the $\Phi$ direction.
Figure 13B:
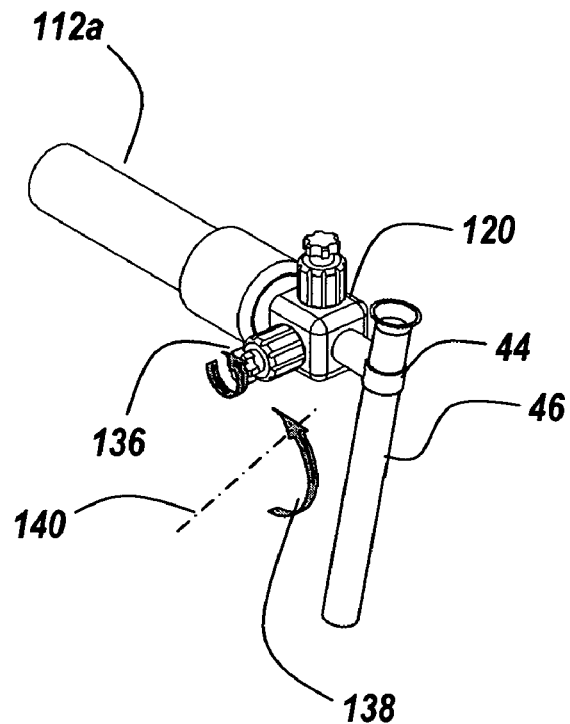
FIG. 13B is a detailed view of the guidance system of FIG. 11 illustrating angular fine adjustment about the $\Psi$ direction.

FIGS. 13A and 13B show detailed views of the illustrative embodiment of the guidance system with a manual angular fine adjustment system. In this illustrative embodiment, the fine adjustment system 120, is configured to rotate the clamp 44 and the cannula 46 about two perpendicular rotations axes. The $\Phi$ fine adjustment control 130 is a knob that, when turned, rotates the clamp 44 and the cannula 46 about the $\Phi$ axis 134. Similarly, turning the $\Psi$ fine adjustment control knob 136 rotates the clamp 44 and the cannula 46 about the $\Psi$ axis 140. The fine adjustment control knob 130 and 136 is connected to a gearing system that converts rotational motion of the knob to rotational motion about a different axis with a magnitude of rotation. The particular rotation mechanism is chosen based on many factors including angular range and desired accuracy. The manual angular fine adjustment system may be implemented using a precision goniometer, which allows pure rotational motion about a "virtual point" external to the goniometer. A standard goniometer can provide 1° resolution with a ±15° range of rotation. Alternatively, the manual angular fine adjustment system may be implemented using precision rotation mounts or stages which can provide greater precision and a larger range of motion.

As shown in FIGS. 12A, 12B, 13A, and 13B, the fine adjustment system includes both angular and linear fine adjustment controls. The knobs consist of two concentric rotational portions. The lower portions of the knobs control linear adjustment 122 and 126 and the upper portions of the knobs control angular adjustment 130 and 136. One of skill in the art will appreciate that the fine adjustment system may include only linear fine adjustments or only rotational fine adjustments. Additionally, the system may include only one angular fine adjustment system and two rotational fine adjustment systems or other combinations.

Figure 14:
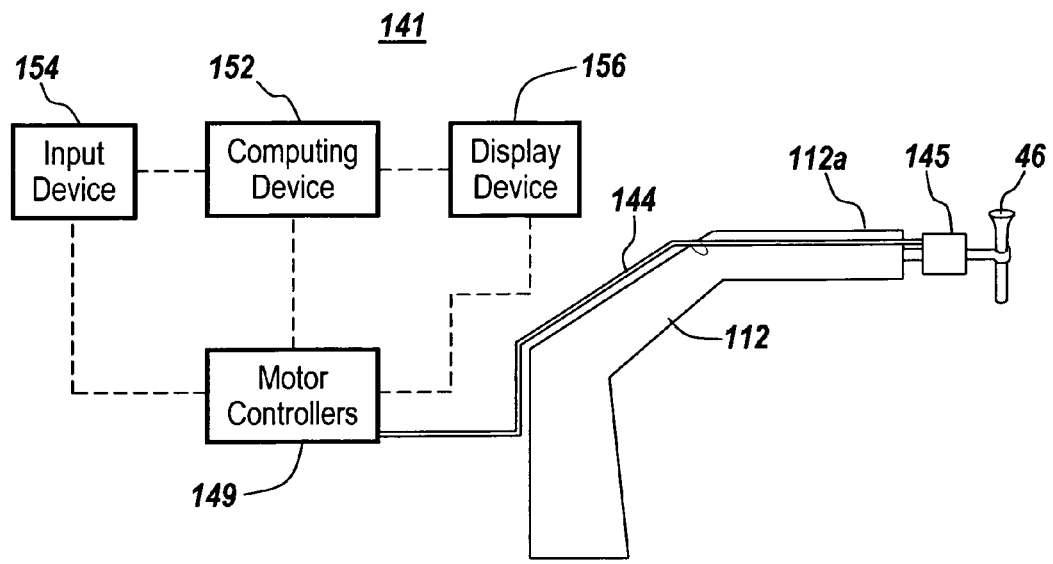
FIG. 14 illustrates a guidance system including a motor-driven mechanical actuation fine adjustment system.

FIG. 14 depicts a different illustrative embodiment of the present invention that incorporates a motor-driven mechanical fine adjustment system. This system is similar to the embodiment shown in FIG. 13, but the mechanical actuators in the fine adjustment system are motor-driven instead of manually actuated. As in the previous embodiment, a moveable support 112 is attached to a stable structure 114 external to the patient and a fine adjustment system is attached to the distal end of the moveable support 112a. In this embodiment, however, the fine adjustment system is a motor-driven mechanical fine adjustment system 141. The motor-driven fine adjustment system has the same physical capabilities and mechanical drive mechanism as a manually actuated system, but it is driven by motors instead of by hand. The motor-driven mechanical actuators 145 may require one or more power or communication cords 144. As shown, the motor-driven mechanical fine adjustment system 141 includes one or more external motor controllers 149. The controllers 149 may be connected to a computing device 152. Alternatively, the controllers 149 could be incorporated into the computing device 152. The motor-driven mechanical fine adjustment system 141 also includes an input device 154 to direct the movement of the motor driven actuators 145. The input device 154 may be a keyboard, a joystick, a mouse, a device for receiving readable media or computer generated instructions, or any other device designed to receive user input. The motor-driven mechanical fine adjustment system 141 may also include a display device 156 for providing feedback and information to the surgeon or operator from the motor controllers 149 and the computing device 152. The feedback may take the form of position, orientation, movement information, position and orientation history, displacement or other relevant information.

Figure 15:
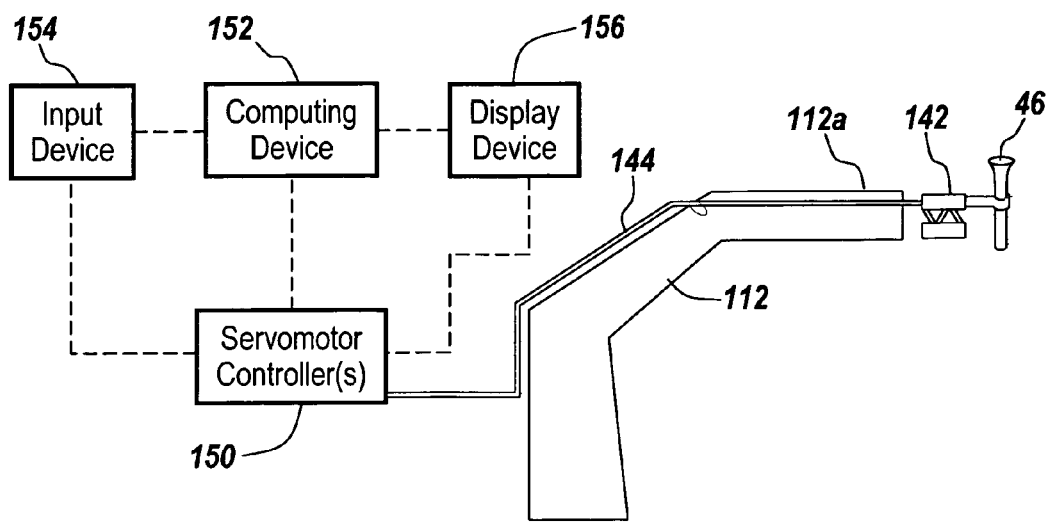
FIG. 15 illustrates a guidance system with a servomotor fine adjustment system according to yet another illustrative embodiment of the invention.

FIG. 15 illustrates yet another different illustrative embodiment of the present invention that incorporates a fine adjustment system with servomotors. As in the previous embodiments, a moveable support 112 is attached to a stable structure 114 external to the patient and a fine adjustment system 142 is attached to the distal end of the moveable support 112*a*. In this embodiment, however, the fine adjustment system is a servomotor system 142. The servomotors are configured to precisely translate and/or rotate the clamp 44 and the cannula 46. The servomotors 142 may require one or more power or communication cords 144. As shown, the servomotor fine adjustment system 142 includes an external servomotor controller 150. Alternatively the controller 150 could be incorporated internally and attached with the servomotors 143 to the distal end of the moveable support 112*a*. The controller 150 may be connected to a computing device 152 as shown in FIG. 14. Alternatively, the controller 150 could be incorporated into the computing device 152. The servomotor system 142 also includes an input device 154 to direct the movement of the servomotor 142. The input device 154 may be a keyboard, a joystick, a mouse, a device for receiving readable media or computer generated instructions, or any other device designed to receive user input. The servomotor system 142 may also include a display device 156 for providing feedback and information to the surgeon or operator from the servomotor controller 150 and the computing device 152. The feedback may take the form of position, orientation, movement information, position and orientation history, displacement or other relevant information.

Figure 16:
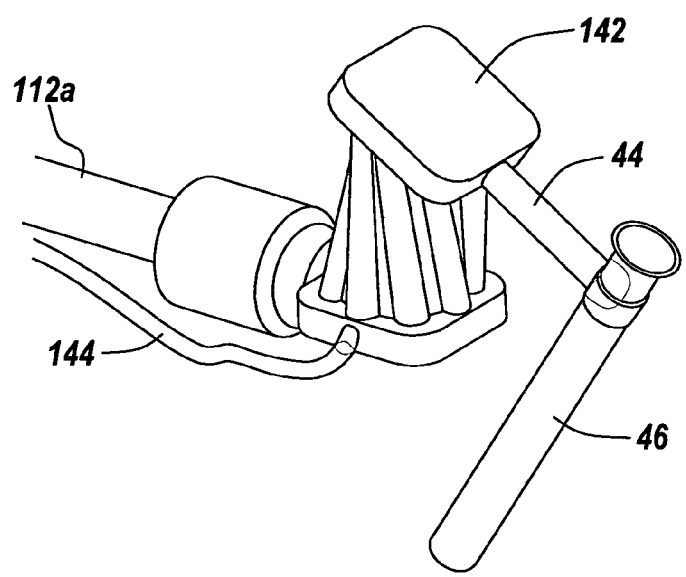
FIG. 16 is a detailed view of the guidance system of FIG. 15 showing the servomotor fine adjustment system.

FIG. 16 shows a detailed view of the guidance system of FIG. 15. The servomotors 142 may be configured to translate the clamp 44 and the cannula 46 linearly in the x, y and z directions. Additionally, the servomotors can be configured to rotate the clamp 44 and the cannula 46 about the Φ and Ψ axes. An electrical cable/connection 144 can be used to supply the servomotors with power and to allow electrical or optical communication between the servomotor controller 150 and the servomotors. The servomotor system may include as many servomotors as required to achieve the desired motion. An individual servomotor converts an electrical voltage to a rotational position of an axle. By combining servomotors both linear and angular positioning may be obtained.

Figure 17:
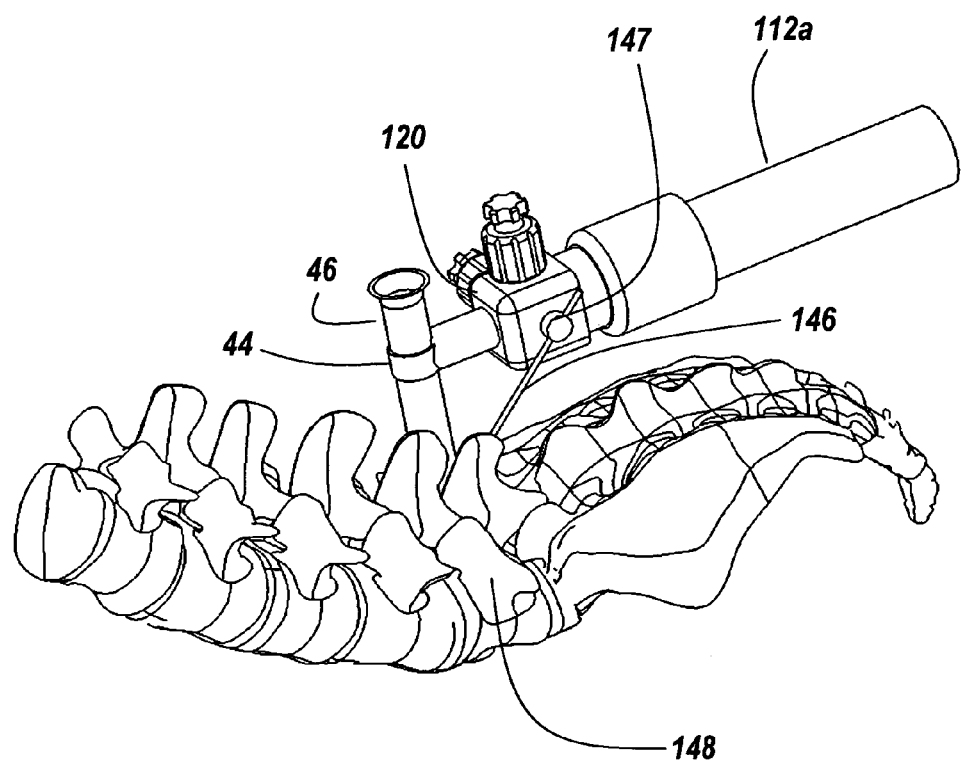
FIG. 17 is a detailed view of the guidance system with a manual fine adjustment system using an anchor to stabilize the position of the trajectory guide.

A detailed view of another illustrative embodiment of a guidance system of the present invention is shown in FIG. 17. This system is similar to the guidance system with manual fine control presented in FIG. 11, with the added feature of stabilization using a bone anchor. This figure shows the fine adjustment system 120 at the distal end of the moveable support 112*a*, being stabilized by contact with an anchoring pin 146. The anchoring pin is attached to a bone in the patient's spine 148. The anchor could be attached to any rigid portion of the patient's body. The fine adjustment system 120 provides an attachment mechanism 147 which is configured to establish a connection between the anchoring pin and the fine adjustment system 120. Although this embodiment shows an anchoring pin 146 connected to the fine adjustment system, one skilled in the art can appreciate that the anchoring element does not need to be a pin and the connection with the anchor may be also established along any portion of the moveable support that would allow for adequate stabilization.

Figure 18:
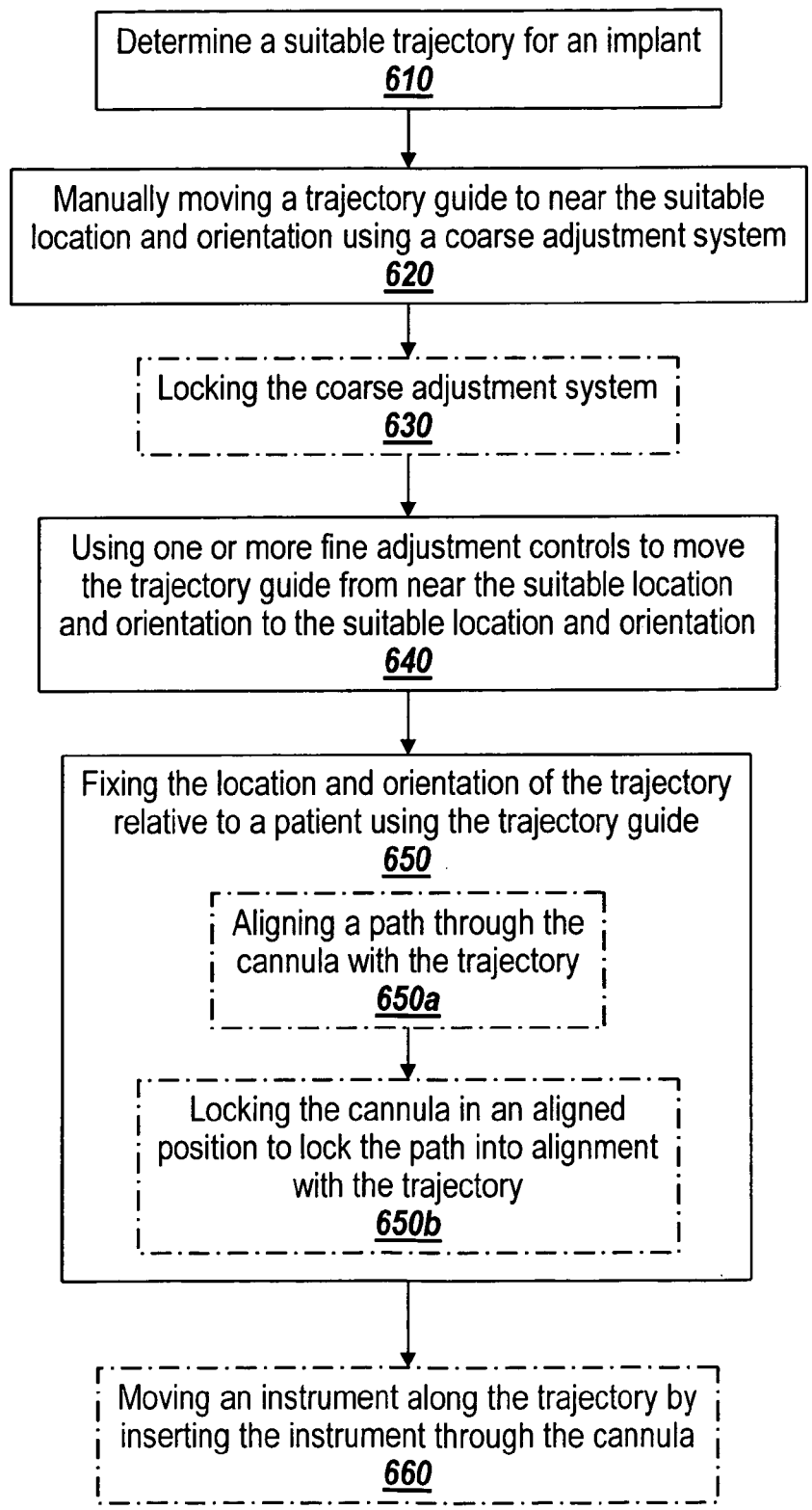
FIG. 18 is a flow chart diagramming the steps involved in using the guidance system of the illustrative embodiment shown in FIG. 11 or 14 to guide instruments and implants into a selected surgical site along a suitable trajectory.

FIG. 18 depicts a flow chart 600 of the steps performed in guiding an implant for a patient. Initially, a suitable trajectory for an implant is determined (step 610). Next, a trajectory guide is manually moved to near the suitable location and orientation using a coarse adjustment system (step 620). The trajectory guide is then moved from near the suitable location and orientation to the suitable location and orientation using one or more fine adjustment controls (step 640). The fine adjustment controls may control a manually actuated system such as a manual micrometer stage, or the fine adjustment controls may control a system actuated by one or more servomotors. The location and orientation of the trajectory relative to a patient is fixed using a trajectory guide (step 650). Several optional steps may be included in this method. After the trajectory guide is manually moved to near the suitable location and orientation using a coarse adjustment system (step 620), the coarse adjustment system may be locked (step 630). The step of fixing the location and orientation of the trajectory relative to a patient using the trajectory guide may include the alignment of a path through the cannula with the trajectory (step 650*a*) and the cannula being locked in an aligned position to lock the path into alignment with the trajectory (step 650*b*). Guiding an implant for a patient may also include the movement of an instrument along the trajectory by inserting the instrument through the cannula (step 660). Although a cannula is specified in steps 650*a* and 650*b* and 660, devices with other shapes that would similarly restrict the motion of an instrument to a defined trajectory could also be used as a trajectory guide.

The present invention has been described relative to illustrative embodiments. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A guidance system for use while inserting an implant, the guidance system comprising:
   a trajectory guide defining a path configured to align with a trajectory for guiding instruments along the trajectory and restricting the instruments to movement along the trajectory, the trajectory guide comprising:
   a cannula extending along a first axis for inserting the instruments in a vertical direction, and
   a clamp connected to the cannula;
   a movable support for moving the clamp of the trajectory guide to a selected position and angular orientation, the moveable support being configured such that the position and angular orientation of the trajectory guide is coarsely adjusted by hand; and
   a fine adjustment system mounted to the movable support and connected to the clamp of the trajectory guide, the fine adjustment system configured to move the clamp of the trajectory guide such that the trajectory guide is aligned precisely with a desired location and orientation, wherein the fine adjustment system includes a first control for translating the clamp and the cannula along a second axis and rotating the clamp and the cannula around a third axis, and a second control for translating the clamp and the cannula along the third axis and rotating the clamp and the cannula around the second axis, the second axis being perpendicular to the third axis, the second and third axes being perpendicular to the first axis, wherein the first control comprises first and second concentric portions, the first concentric portion controlling translation of the clamp and the cannula along the second axis, the second concentric portion controlling rotation of the clamp and the cannula around the third axis, wherein the second control comprises third and fourth concentric portions, the third concentric portion controlling translation of the clamp and the cannula along the third axis, the fourth concentric portion controlling rotation of the clamp and the cannula around the second axis.

2. The guidance system of claim 1, further comprising:
a lock for locking the trajectory guide in the desired location and orientation relative to a patient.

3. The guidance system of claim 2, wherein the lock comprises one of a set screw, a clamp, a collet, a friction lock, an electronic lock, a mechanical lock an electromechanical locks and a pneumatic lock.

4. The guidance system of claim 1, wherein the moveable support is configured such that the moveable support maintains a fixed location and orientation in the absence of additional external applied force when not locked down.

5. The guidance system of claim 1, wherein the fine adjustment system is a manually actuated system.

6. The guidance system of claim 1, wherein the fine adjustment system comprises at least one manually controlled linear micrometer.

7. The guidance system of claim 1, wherein the fine adjustment system comprises at least one manually controlled goniometer.

8. The guidance system to claim 1, wherein the fine adjustment system is configured to move the trajectory guide in at least two perpendicular linear directions.

9. The guidance system of claim 1, wherein the fine adjustment system is configured to move the trajectory guide through angles about two perpendicular rotation axes.

10. The guidance system of claim 1, wherein the trajectory guide comprises a cannula.

11. The guidance system of claim 1, wherein the moveable support is adapted to contact an anchor which is attached to a rigid portion of a patient body and wherein contact with the anchor stabilizes a location of the moveable support.

12. A fine adjustment guidance system for use while inserting an implant, the fine adjustment guidance system comprising:

a trajectory guide defining a path configured to align with a trajectory for guiding instruments along the trajectory and restricting the instruments to movement along the trajectory, the path extending along a first axis for inserting the instrument in a vertical direction, an end of the trajectory guide being configured to engage a bone in a patient body; and a fine adjustment system configured to be mounted on a moveable support and connected to the trajectory guide to align the trajectory guide precisely with a desired location and orientation, wherein the fine adjustment system includes a first control means for translating the trajectory guide along a second axis and rotating the trajectory guide around a third axis, and a second control means for translating the trajectory guide along the third axis and rotating the trajectory guide around the second axis, the second axis being perpendicular to the second axis, the second and third axes being perpendicular to the first axis, wherein the first control means comprises first and second concentric portions, the first concentric portion controlling translation of the clamp and the cannula along the second axis, the second concentric portion controlling rotation of the clamp and the cannula around the third axis, wherein the second control means comprises third and fourth concentric portions, the third concentric portion controlling translation of the clamp and the cannula along the third axis, the fourth concentric portion controlling rotation of the clamp and the cannula around the second axis.

* * * * *